US012661443B2

(12) United States Patent
Locke et al.

(10) Patent No.: US 12,661,443 B2
(45) Date of Patent: Jun. 23, 2026

(54) CONTRACTIBLE DRESSING MANIFOLD WITH REDUCED TISSUE IN-GROWTH

(71) Applicant: KCI Manufacturing Unlimited Company, Westmeath (IE)

(72) Inventors: Christopher Brian Locke, San Antonio, TX (US); Timothy Mark Robinson, San Antonio, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 448 days.

(21) Appl. No.: 18/036,607

(22) PCT Filed: Nov. 11, 2021

(86) PCT No.: PCT/IB2021/060447
§ 371 (c)(1),
(2) Date: May 11, 2023

(87) PCT Pub. No.: WO2022/118117
PCT Pub. Date: Jun. 9, 2022

(65) Prior Publication Data
US 2024/0016995 A1 Jan. 18, 2024

Related U.S. Application Data

(60) Provisional application No. 63/119,890, filed on Dec. 1, 2020.

(51) Int. Cl.
*A61M 1/00* (2006.01)
*A61F 13/01* (2024.01)
*A61F 13/05* (2024.01)

(52) U.S. Cl.
CPC ....... *A61M 1/915* (2021.05); *A61F 13/01021* (2024.01); *A61F 13/01042* (2024.01); *A61F 13/05* (2024.01)

(58) Field of Classification Search
CPC ............ A61F 13/05; A61F 2013/00544; A61F 2013/00578; A61M 1/905
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Philip R Wiest
*Assistant Examiner* — Meagan Ngo

(57) ABSTRACT

Some examples of a dressing for treating a tissue site can include a manifold layer comprised of foam. The manifold layer can have a first side, a second side, and a thickness between the first side and the second side. The manifold layer can include a plurality of holes extending through the thickness of the manifold layer and being positioned at least in a first row and a second row. Each of the plurality of holes may have a hole length that is longer than and perpendicular to a hole width. The hole length of at least one of the holes in the first row may be positioned at an angle relative to the hole length of another of the holes in the second row. The manifold layer can be configured to prevent tissue in-growth (Continued)

and contract radially in all directions. Other apparatuses, dressings, systems, and methods are disclosed.

25 Claims, 15 Drawing Sheets

(56)                    References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0069858 A1* | 3/2010 | Olson ................... A61M 1/915 |
| | | 604/319 |
| 2012/0041402 A1* | 2/2012 | Greener .................. A61F 13/05 |
| | | 83/13 |
| 2012/0330253 A1* | 12/2012 | Robinson ................ A61F 13/05 |
| | | 604/319 |
| 2014/0163491 A1 | 6/2014 | Schuessler et al. |
| 2015/0080788 A1 | 3/2015 | Blott et al. |
| 2015/0209200 A1* | 7/2015 | Fouillet ............... A61F 13/0213 |
| | | 604/378 |
| 2015/0245949 A1* | 9/2015 | Locke ................. A61F 13/0283 |
| | | 156/244.18 |
| 2015/0320602 A1* | 11/2015 | Locke ............... A61F 13/01017 |
| | | 606/213 |
| 2016/0022885 A1* | 1/2016 | Dunn .................... A61F 13/022 |
| | | 604/319 |
| 2018/0353341 A1* | 12/2018 | Locke ................... A61M 1/962 |
| 2019/0240073 A1* | 8/2019 | Allen ..................... A61F 13/05 |
| 2019/0307935 A1* | 10/2019 | Simmons ............. B29C 51/268 |
| 2020/0107965 A1 | 4/2020 | Greener |
| 2020/0121509 A1 | 4/2020 | Locke et al. |
| 2020/0146896 A1 | 5/2020 | Rice et al. |

(56) References Cited

U.S. PATENT DOCUMENTS

| | | | | | |
|---|---|---|---|---|---|
| 2021/0106737 A1* | 4/2021 | Obst | | | A61M 1/90 |
| 2021/0137746 A1* | 5/2021 | Dutta | | | A61M 1/90 |

FOREIGN PATENT DOCUMENTS

| | | | |
|---|---|---|---|
| AU | 755496 | B2 | 12/2002 |
| CA | 2005436 | A1 | 6/1990 |
| DE | 26 40 413 | A1 | 3/1978 |
| DE | 43 06 478 | A1 | 9/1994 |
| DE | 29 504 378 | U1 | 9/1995 |
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 1018967 | A1 | 7/2000 |
| GB | 692578 | A | 6/1953 |
| GB | 2195255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract,

(56) References Cited

OTHER PUBLICATIONS editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

International Search Report and Written Opinion corresponding to International Application PCT/IB2021/060447, Mailed Feb. 18, 2022.

* cited by examiner

BEFORE VACUUM

|  | INCLINED OVAL | STAR | PARALLELOGRAM | PARALLELOGRAM (OVERLAPPING PERFORATIONS) | GENERIC FOAM (NO HOLES) |
|---|---|---|---|---|---|
| LENGTH (mm) | 192 | 170 | 172 | 172 | 177 |
| WIDTH (mm) | 97 | 120 | 112 | 112 | 117 |
| AREA | 18624 | 20400 | 19264 | 19264 | 20709 |

AFTER VACUUM (125mm Hg)

|  | INCLINED OVAL | STAR | PARALLELOGRAM | PARALLELOGRAM (OVERLAPPING PERFORATIONS) | GENERIC FOAM (NO HOLES) |
|---|---|---|---|---|---|
| LENGTH (mm) | 170 | 160 | 154 | 152 | 160 |
| WIDTH (mm) | 85 | 110 | 85 | 83 | 107 |
| AREA | 14450 | 17600 | 13090 | 12616 | 17120 |
| RETAINED AREA | 0.78 | 0.86 | 0.68 | 0.65 | 0.83 |
| % COLLAPSE | 22.41 | 13.73 | 32.05 | 34.51 | 17.33 |

FIG. 10

CONTRACTIBLE DRESSING MANIFOLD WITH REDUCED TISSUE IN-GROWTH

CROSS-REFERENCE TO RELATED APPLICATIONS

This application claims the benefit of priority to U.S. Provisional Application No. 63/119,890 filed on Dec. 1, 2020, which is incorporated herein by reference in its entirety.

TECHNICAL FIELD

The invention set forth in the appended claims relates generally to tissue treatment systems and more particularly, but without limitation, to dressings for tissue treatment and methods of using the dressings for tissue treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative example embodiments are also provided to enable a person skilled in the art to make and use the claimed subject matter.

For example, in some example embodiments, a dressing for treating tissue may include a manifold layer having a first side configured to face the tissue site, a second side opposite the first side, and a thickness between the first side and the second side. The manifold can be a foam having a 25% compression load deflection between about 1.8 to about 2.8 pounds per square inch and pores having an average pore size between about 50 microns to about 120 microns. The dressing can also have a plurality of holes extending through the first side, the second side, and the thickness of the manifold layer. The holes can be positioned at least in a first row and a second row that is offset from the first row. Each of the plurality of holes can include a hole length that is longer than and perpendicular to a hole width. The hole length of at least one of the holes in the first row can be positioned at an angle relative to the hole length of another of the holes in the second row.

Some embodiments of a dressing for treating a tissue site with negative pressure can include a manifold layer comprising a foam. The manifold layer can have a first side configured to face the tissue site, a second side opposite the first side, and a thickness between the first side and the second side. In some embodiments, the dressing can include a plurality of holes extending through the first side, the second side, and the thickness of the manifold layer. The plurality of holes can be positioned at least in a first row and a second row that is offset from the first row. Each of the plurality of holes can include a hole length that is longer than and perpendicular to a hole width. The hole length of at least one of the holes in the first row can be positioned at an angle relative to the hole length of another of the holes in the second row. In some embodiments, the dressing can also include at least one surface channel having a channel length extending along at least one manifold surface of the manifold layer. The at least one surface channel can have a channel depth and a channel width perpendicular to the channel length. The channel depth can extend into the thickness of the manifold layer from the manifold surface and the channel width can extend perpendicular to the channel depth.

Some embodiments of a dressing for treating a tissue site with negative pressure can include a manifold layer comprised of a foam. The manifold layer can include a first side configured to face the tissue site, a second side opposite the first side, and a thickness between the first side and the second side. In some embodiments, the dressing can also have a plurality of holes extending through the first side, the second side, and the thickness of the manifold layer. The plurality of holes can be positioned at least in a first row and a second row. Each of the plurality of holes can include a hole length that is longer than and perpendicular to a hole width. The hole length of at least one of the holes in the first row can be positioned at an angle relative to the hole length of another of the holes in the second row. The manifold layer of the dressing can also be configured to prevent tissue in-growth and to contract radially in all directions in a contraction plane.

Some embodiments of a system for treating a tissue site with reduced pressure can include a dressing according to this disclosure. The system can include a cover configured to create a sealed space containing the manifold layer at the tissue site. The system can also include a reduced-pressure source configured to be positioned in fluid communication with the sealed space and the manifold layer through the cover.

Other objectives, advantages, and a preferred mode of making and using the claimed subject matter may be understood best by reference to the accompanying drawings in conjunction with the following detailed description of illustrative example embodiments.

BRIEF DESCRIPTION OF THE DRAWINGS

FIG. 10 is a table illustrating an improved percentage of collapse of a tissue interface according to this disclosure.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

Figure 1:
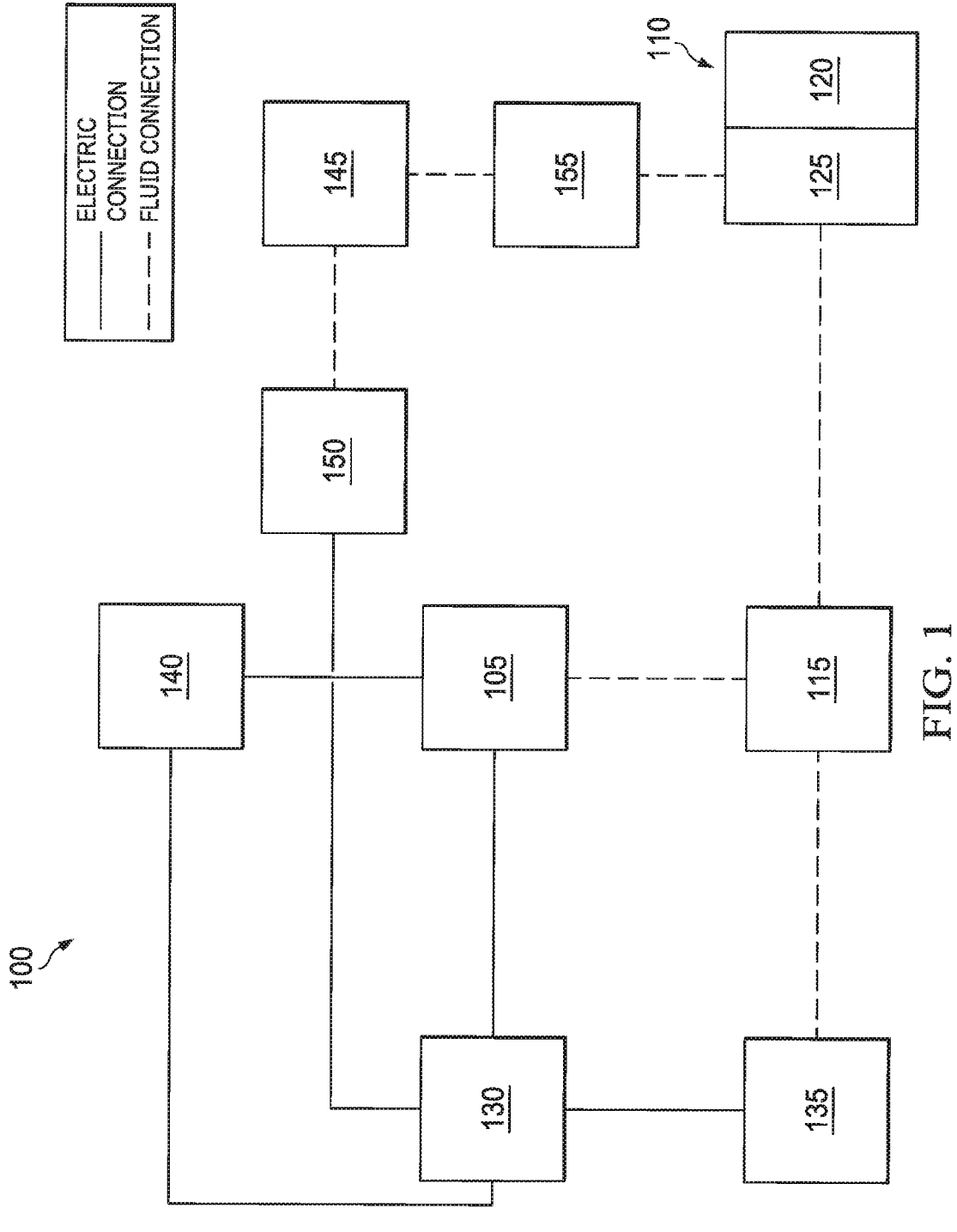
FIG. 1 is a block diagram of an example embodiment of a therapy system and a dressing that can provide negative-pressure treatment and instillation treatment in accordance with this specification.

FIG. 1 is a block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on a body that is exposed to the external environment, such as an injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may include a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source, such as a positive-pressure source 150, a negative-pressure source such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may include or may be a manifold. A manifold in this context may include a means for collecting or distributing fluid across or through the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may be, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may be, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polyamide copolymers. Such materials are commercially available as, for example, Tegaderm® drape, commercially available from 3M Company, Minneapolis Minnesota; polyurethane (PU) drape; polyether block polyamide copolymer (PEBAX), for example; and INSPIRE 2301 and INSPIRE 2327 polyurethane films, commercially available from Expopack Advanced Coatings, Wrexham, United Kingdom. In some embodiments, the cover 125 may comprise INSPIRE 2301 having an MVTR (upright cup technique) of 2600 g/m²/24 hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

In general, exudate and other fluid flow toward lower pressure along a fluid path. Thus, the term "downstream" may refer to a location in a fluid path relatively closer to a source of negative pressure or further away from a source of positive pressure. Conversely, the term "upstream" may refer to a location further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

In some embodiments, the controller 130 may have a continuous pressure mode, in which the negative-pressure source 105 is operated to provide a constant target negative pressure for the duration of treatment or until manually deactivated. Additionally or alternatively, the controller may have an intermittent pressure mode. For example, the controller 130 can operate the negative-pressure source 105 to cycle between a target pressure and atmospheric pressure. For example, the target pressure may be set at a value of 135 mmHg for a specified period of time (e.g., 5 min), followed by a specified period of time (e.g., 2 min) of deactivation. The cycle can be repeated by activating the negative-pressure source 105, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time. The initial rise time may vary depending on the type of dressing and therapy equipment being used. For example, some therapy systems may increase negative pressure at a rate of about 20-30 mmHg/second, and other therapy systems may increase negative pressure at a rate of about 5-10 mmHg/second. If the therapy system 100 is operating in an intermittent mode, the repeating rise time may be a value substantially equal to the initial rise time.

In some example dynamic pressure control modes, the target pressure can vary with time. For example, the target pressure may vary in the form of a triangular waveform, varying between a negative pressure of 50 and 135 mmHg with a rise rate of negative pressure set at a rate of 25 mmHg/min. and a descent rate set at 25 mmHg/min. In other embodiments of the therapy system 100, the triangular waveform may vary between negative pressure of 25 and 135 mmHg with a rise rate of about 30 mmHg/min and a descent rate set at about 30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

In some embodiments, the controller 130 may receive and process data, such as data related to instillation solution provided to the tissue interface 120. Such data may include the type of instillation solution prescribed by a clinician, the volume of fluid or solution to be instilled to a tissue site ("fill volume"), and the amount of time prescribed for leaving solution at a tissue site ("dwell time") before applying a negative pressure to the tissue site. The fill volume may be, for example, between 10 and 500 mL, and the dwell time may be between one second to 30 minutes. The controller 130 may also control the operation of one or more components of the therapy system 100 to instill solution. For example, the controller 130 may manage fluid distributed from the solution source 145 to the tissue interface 120. In some embodiments, fluid may be instilled to a tissue site by applying a negative pressure from the negative-pressure source 105 to reduce the pressure at the tissue site, drawing solution into the tissue interface 120. In some embodiments, solution may be instilled to a tissue site by applying a positive pressure from the positive-pressure source 150 to move solution from the solution source 145 to the tissue interface 120. Additionally or alternatively, the solution source 145 may be elevated to a height sufficient to allow gravity to move solution into the tissue interface 120.

The controller 130 may also control the fluid dynamics of instillation by providing a continuous flow of solution or an intermittent flow of solution. Negative pressure may be applied to provide either continuous flow or intermittent flow of solution. The application of negative pressure may be implemented to provide a continuous pressure mode of operation to achieve a continuous flow rate of instillation solution through the tissue interface 120, or it may be implemented to provide a dynamic pressure mode of operation to vary the flow rate of instillation solution through the tissue interface 120. Alternatively, the application of negative pressure may be implemented to provide an intermittent mode of operation to allow instillation solution to dwell at the tissue interface 120. In an intermittent mode, a specific fill volume and dwell time may be provided depending, for example, on the type of tissue site being treated and the type of dressing being utilized. After or during instillation of solution, negative-pressure treatment may be applied. The controller 130 may be utilized to select a mode of operation and the duration of the negative pressure treatment before commencing another instillation cycle.

Some dressings can be worn for a time period extending beyond seven days, which can be referred to as an extended wear time. Dressings for extended wear time can provide cost-savings, time-efficiencies, and less trauma to a patient during dressing changes. Some highly felted foam materials may be worn for an extended period of time without suffering tissue in-growth. However, some felted foam materials may be quite stiff. Stiffer foam materials may be hard to conform, difficult to resize, and unable to collapse under negative pressure to provide macro-strain to the tissue site. Additionally the stiff foam material may not efficiently deliver fluid and pressure to the tissue site because the manifold is unable to contract radially.

These limitations and others may be addressed by the therapy system 100, which can provide negative-pressure therapy and installation therapy. In some embodiments, the therapy system 100 may include a tissue interface or manifold layer that can prevent tissue-ingrowth but is also flexible, collapsible, and resizable. The tissue interface or manifold layer may include a pattern enabling the manifold to contract radially in all directions, thereby increasing the effectiveness of the therapy system 100.

Figure 2A:
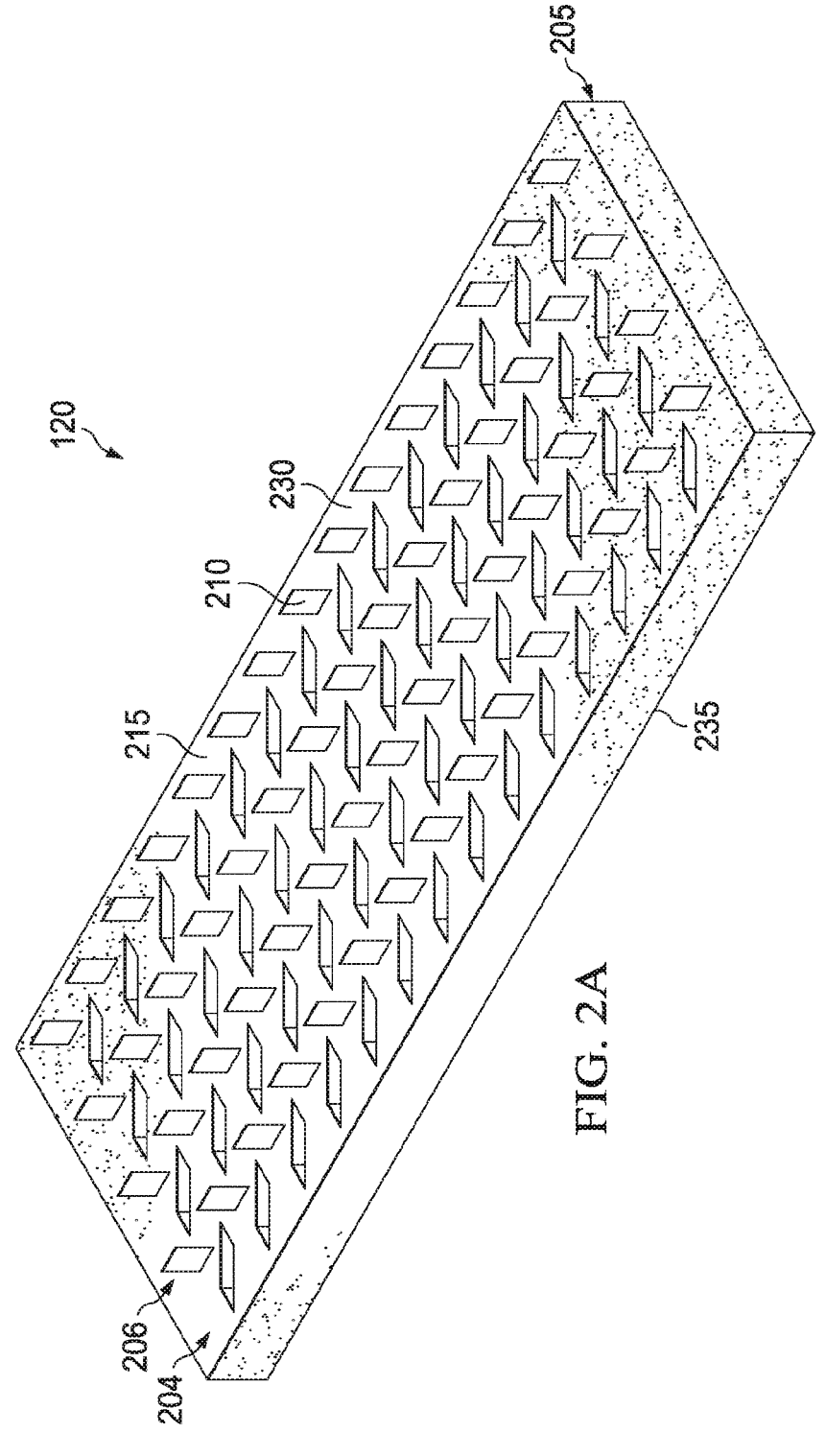
FIG. 2A is a perspective view of an example of a tissue interface that can be associated with some embodiments of the therapy system and the dressing of FIG. 1.

FIG. 2A is a perspective view of an example of the tissue interface 120 of FIG. 1, illustrating additional details that may be associated with some embodiments. Herein, various examples of the tissue interface 120 are described that may be suitable for use with the dressing 110 and the therapy system 100. Further, features or elements of the tissue interface 120 described herein may be referred to as part of the therapy system 100 or the dressing 110 without reference to the tissue interface 120.

In the example of FIG. 2A, the tissue interface 120 may include or may be a manifold, such as a manifold layer 205. The manifold layer 205 may also provide a means for collecting or distributing fluid across the tissue interface 120 under pressure. For example, the manifold layer 205 may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as from a source of installation solution, across the tissue interface 120.

In some illustrative embodiments, the pathways of the manifold layer 205 may be interconnected to improve distribution or collection of fluids. In some illustrative embodiments, the manifold layer 205 may be a porous material having interconnected fluid pathways. Examples of suitable porous material that comprise or can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, the manifold layer 205 may additionally or alternatively include projections that form interconnected fluid pathways. For example, the manifold layer 205 may be molded to provide surface projections that define interconnected fluid pathways.

In some embodiments, the manifold layer 205 may be a foam having pore sizes that may vary according to needs of a prescribed therapy. For example, a foam having an average pore size in a range of 50-120 microns may be particularly suitable for some types of therapy. The tensile strength of the manifold layer 205 may also vary according to needs of a prescribed therapy. For example, the tensile strength of a foam may be increased for instillation of topical treatment solutions. In some embodiments, the manifold layer 205 may have a 25% compression load deflection of about 1.8 to about 2.8 pounds per square inch, and a 65% compression load deflection of about 2.2 to about 3.4 pounds per square inch. In some embodiments, the manifold layer 205 may be a foam comprised of polyols such as polyester or polyether, isocyanate such as toluene diisocyanate, and polymerization modifiers such as amines and tin compounds. In some examples, the manifold layer 205 may be a reticulated polyurethane foam such as used in GRANUFOAM™ Dressing or V.A.C. VERAFLO™ Dressing, both available from KCI of San Antonio, Texas.

In some embodiments, the manifold layer 205 may be formed by a felting process. Any porous foam suitable for felting may be used, including the example foams mentioned herein, such as GRANUFOAM™ Dressing. Felting comprises a thermoforming process that permanently compresses a foam to increase the density of the foam while maintaining interconnected pathways. Felting may be performed by any known methods, which may include applying heat and pressure to a porous material or foam material. Some methods may include compressing a foam blank between one or more heated platens or dies (not shown) for a specified period of time and at a specified temperature. The direction of compression may be along the thickness of the foam blank.

The period of time of compression may range from 10 minutes up to 24 hours, though the time period may be more or less depending on the specific type of porous material used. Further, in some examples, the temperature may range between 120° C. to 260° C. Generally, the lower the temperature of the platen, the longer a porous material must be held in compression. After the specified time period has elapsed, the pressure and heat will form a felted structure or surface on or through the porous material or a portion of the porous material.

The felting process may alter certain properties of the original material, including pore shape and/or size, elasticity, density, and density distribution. For example, struts that define pores in the foam may be deformed during the felting process, resulting in flattened pore shapes. The deformed struts can also decrease the elasticity of the foam. The density of the foam is generally increased by felting. In some embodiments, contact with hot-press platens in the felting process can also result in a density gradient in which the density is greater at the surface and the pores size is smaller at the surface. In some embodiments, the felted structure may be comparatively smoother than any unfinished or non-felted surface or portion of the porous material. Further, the pores in the felted structure may be smaller than the pores throughout any unfinished or non-felted surface or portion of the porous material. In some examples, the felted structure may be applied to all surfaces or portions of the porous material. Further, in some examples, the felted structure may extend into or through an entire thickness of the porous material such that all of the porous material is felted.

A felted foam may be characterized by a firmness factor, which is indicative of the compression of the foam. The firmness factor of a felted foam can be specified as the ratio of original thickness to final thickness. A compressed or felted foam may have a firmness factor greater than 1. The degree of compression may affect the physical properties of the felted foam. For example, felted foam has an increased effective density compared to a foam of the same material that is not felted. The felting process can also affect fluid-to-foam interactions. For example, as the density increases, compressibility or collapse may decrease. Therefore, foams which have different compressibility or collapse may have different firmness factors. In some example embodiments, a firmness factor can range from about 2 to about 10. For example, the firmness factor of the manifold layer 205 felted foam may be about 5 to 8 in some embodiments. There is a general linear relationship between firmness level, density, pore size (or pores per inch) and compressibility. For example, foam that is felted to a firmness factor of 5 will show a five-fold density increase and compress to about a fifth of its original thickness.

In some embodiments, the manifold layer 205 may be a closed-cell foam such as, for example, those manufactured by Zotefoams, Inc. of Walton, Kentucky, U.S.A., including the Azote, Plastazote, Evazote, Supazote, and Zotek grades. Such closed-cell foams may be manufactured by extruding polymer sheets or blocks and crosslinking through high energy radiation. Suitable polymers may include low and high density polyolefins and copolymers with vinyl acetate, fluoropolymers, polyamides, and PEBAX. The polymer sheets may then be softened under heat and exposed to high pressure nitrogen gas which dissolves in the polymer. After cooling, the polymer sheets may be heated again and exposed to subatmospheric pressure, resulting in expansion and formation of the closed-cell foam. In some embodiments, the closed-cell foam may be thermoformed. Thermoforming the foam involves embossing patterns and structures, such as channels, into the surfaces of the foam in order to translate what would otherwise be non-manifolding material into a structure that will manifold pressure and fluid along the channels.

In some embodiments, one or more suitable foam blanks may be used for forming the manifold layer 205. The foam blanks may be open cell foam, felted foam, closed cell foam, or another foam as described herein. However, the properties of any of these foam blanks may have about 200 to about 400 pores per inch on average, a density of about 6.5 to about 12.8 lb/ft$^3$, a free volume of about 90% or more, an average pore size in a range of about 50 to about 120 microns, and/or a 25% compression load deflection of at least 1.5 pounds per square inch. In some embodiments, the foam blank(s) may have a thickness greater than 8 millimeters, for example 8-16 millimeters.

As further shown in FIG. 2A, the manifold layer 205 may comprise one or more holes 210 extending through a first side 230, a second side 235 opposite the first side 230, and a thickness of the manifold layer 205. The thickness of the manifold layer 205 may be between about 8-16 millimeters. The plurality of holes 210 may be distributed uniformly or randomly across the manifold layer 205. In some embodiments, the plurality of holes 210 may be positioned in at least a first row 204 and a second row 206 that is offset or staggered from the first row 204. The plurality of holes 210 extending through the manifold layer 205 may form a plurality of walls 215 extending through the manifold layer 205. The holes 210 may be configured to contract radially in all directions in response to the application of negative pressure to the tissue interface 120 such that there is radial mechanical deformation at the tissue site.

In some embodiments, the holes 210 may be formed during molding of the manifold layer 205. In other embodiments, the holes 210 may be formed by cutting, melting, or vaporizing the manifold layer 205. For example, the holes 210 may be formed in the manifold layer 205 by laser cutting the felted foam of the manifold layer 205.

Figure 2B:
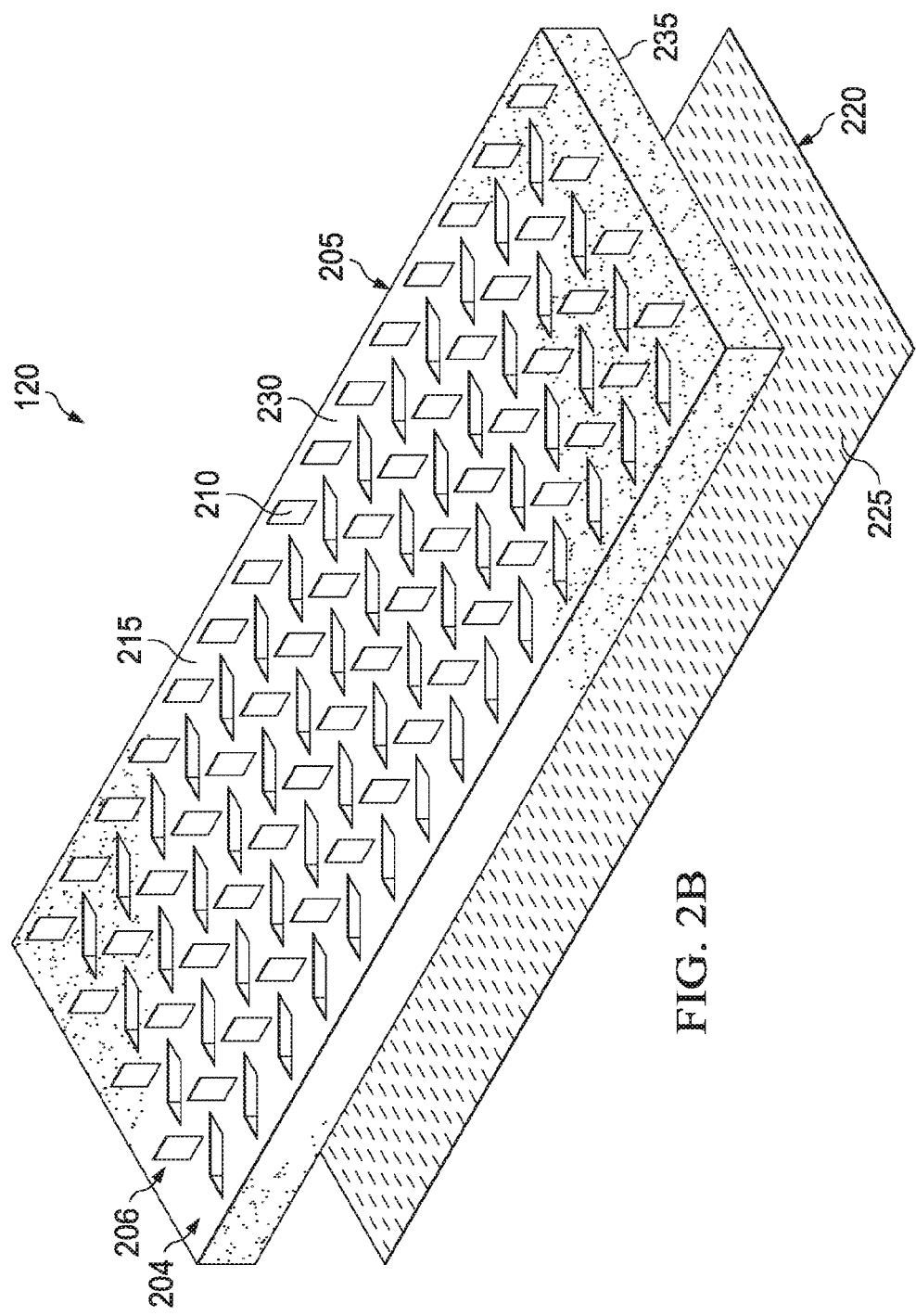
FIG. 2B is an exploded view of an example of a tissue interface that can be associated with some embodiments of the therapy system and the dressing of FIG. 1.

FIG. 2B is an exploded view of another example of the tissue interface 120 of FIG. 1, illustrating additional details that may be associated with some embodiments. In some embodiments, the tissue interface 120 may comprise the manifold layer 205 and an optional contact layer 220. In some embodiments, the contact layer 220 may optionally be disposed adjacent to the manifold layer 205. For example, the contact layer 220 and the manifold layer 205 may be stacked so that the contact layer 220 is in contact with the manifold layer 205. The contact layer 220 may also be heat-bonded or adhered to the manifold layer 205 in some embodiments, for example, using hot melt adhesive. In some embodiments, the contact layer 220 may optionally include a low-tack adhesive, which can be configured to hold the tissue interface 120 in place while the cover 125 is applied. The low-tack adhesive may be continuously coated on the contact layer 220 or applied in a pattern. In some embodiments, the contact layer 220 may be configured to be positioned between the manifold layer 205 and a tissue site. In some embodiments, the contact layer 220 may be configured to be positioned in direct contact with the tissue site. The contact layer 220 can provide additional protection to the epidermis from irritation that could be caused by expansion, contraction, or other movement of the manifold layer 205. The contact layer 220 can also reduce tissue in-growth into the manifold layer 205.

The contact layer 220 may include a means for controlling or managing fluid flow. In some embodiments, the contact layer 220 may be a fluid control layer comprising a liquid-impermeable, elastomeric material. For example, the contact layer 220 may be a polymer film, such as a polyurethane film. In some embodiments, the contact layer 220 may be the same material as the cover 125. The contact layer 220 may also have a smooth or matte surface texture in some embodiments. A glossy or shiny finish finer or equal to a grade B3 according to the SPI (Society of the Plastics Industry) standards may be particularly advantageous for some applications. In some embodiments, variations in surface height may be limited to acceptable tolerances. For example, the surface of the contact layer 220 may have a substantially flat surface, with height variations limited to 0.2 millimeters over a centimeter.

In some embodiments, the contact layer 220 may be hydrophobic. The hydrophobicity of the contact layer 220 may vary, but may have a contact angle with water of at least ninety degrees in some embodiments. In some embodiments the contact layer 220 may have a contact angle with water of no more than 150 degrees. For example, in some embodiments, the contact angle of the contact layer 220 may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTÅ125, FTÅ200, FTÅ2000, and FTÅ4000 systems, all commercially available from First Ten Angstroms, Inc., of Portsmouth, VA, and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles herein represent averages of 5-9 measured values, discarding both the highest and lowest measured values. The hydrophobicity of the contact layer 220 may be further enhanced with a hydrophobic coating of other materials, such as silicones and fluorocarbons, either as coated from a liquid, or plasma coated.

The contact layer 220 may also be suitable for welding to other layers, including the manifold layer 205. For example, the contact layer 220 may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene. In some embodiments, the contact layer 220 may be flame laminated to the manifold layer 205.

The area density of the contact layer 220 may vary according to a prescribed therapy or application. In some embodiments, an area density of less than 40 grams per square meter may be suitable, and an area density of about 20-30 grams per square meter may be particularly advantageous for some applications.

In some embodiments, for example, the contact layer 220 may be a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styreneics, silicones, fluoropolymers, and acetates. A thickness between 20 microns and 100 microns may be suitable for many applications. Films may be clear, colored, or printed. More polar films suitable for laminating to a polyethylene film include polyimide, copolyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

The contact layer 220 may have one or more passages, which can be distributed uniformly or randomly across the contact layer 220. In some embodiments, the passages may be bi-directional and pressure-responsive. For example, each of the passages generally may be an elastic passage that is normally unstrained to substantially reduce liquid flow, and can expand or open in response to a pressure gradient and/or in response to the contraction of the manifold layer 205. As illustrated in the example of FIG. 2B, the passages may be a plurality of perforations 225 disposed through opposing surfaces of the contact layer 220. The plurality of perforations 225 may be formed by removing material from the contact layer 220. For example, the plurality of perforations 225 may be formed by cutting through the contact layer 220. In the absence of a pressure gradient across the plurality of perforations 225, the plurality of perforations 225 may be sufficiently small to form a seal or fluid restriction, which can substantially reduce or prevent liquid flow. Additionally, or alternatively, one or more of the passages may be or may function as an elastomeric valve that is normally closed when unstrained to substantially prevent liquid flow, and can open in response to a pressure gradient and/or in response to the contraction of the manifold layer 205. In some examples, the passages may be fenestrations in the contact layer 220. Generally, fenestrations are a species of perforation, and may also be formed by removing material from the contact layer 220. The amount of material removed and the resulting dimensions of the fenestrations may be up to an order of magnitude less than perforations.

In some embodiments, the plurality of perforations 225 may be formed as slots (or fenestrations formed as slits) in the contact layer 220. In some examples, the plurality of perforations 225 may be linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications, and a tolerance of about 0.1 millimeter may also be acceptable. Such dimensions and tolerances may be achieved with a laser cutter, for example. Slots of such configurations may function as imperfect elastomeric valves that can substantially reduce liquid flow in a normally closed or resting state. For example, such slots may form a flow restriction without being completely closed or sealed. The slots can expand or open wider in response to a pressure gradient and/or in response to the contraction of the manifold layer 205 to allow increased liquid flow.

Figure 3A:
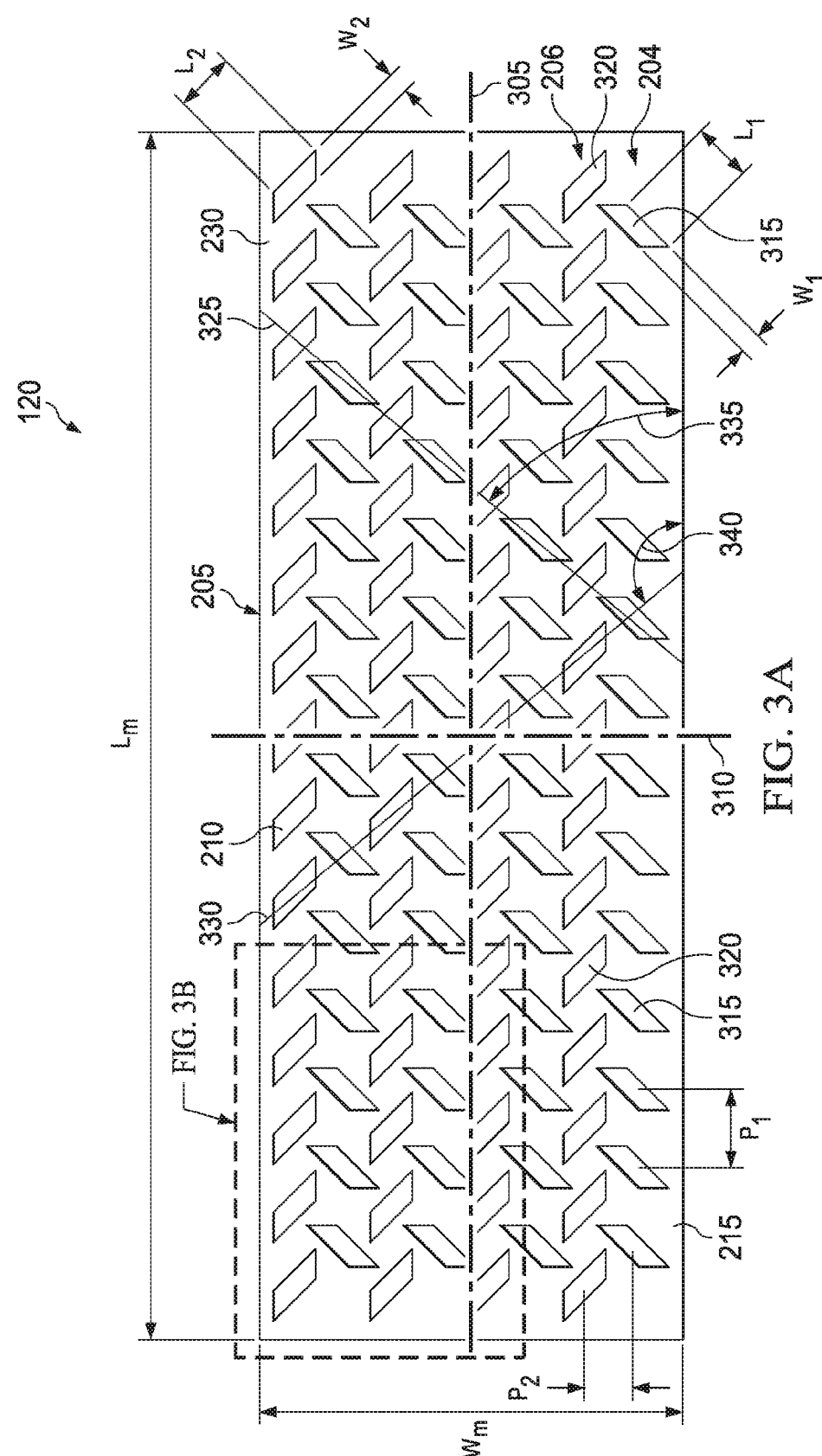
FIG. 3A is a top view of the tissue interface of FIG. 2A.

FIG. 3A is a top view of the tissue interface of FIG. 2A, illustrating additional details that may be associated with some embodiments. As shown in FIG. 3A, in some embodiments, the tissue interface 120 may have a first orientation line 305 and a second orientation line 310 that is perpendicular to the first orientation line 305. In some embodiments, the first orientation line 305 may be parallel to a length LAI of the tissue interface 120 and the manifold layer 205, and the second orientation line 310 may be parallel to a width $W_M$ of the tissue interface 120 and the manifold layer 205. Generally, the first orientation line 305 and the second orientation line 310 aid in the description of the tissue interface 120.

In some embodiments, the manifold layer 205 may be configured to contract radially in all directions in a plane under the application of negative pressure. For example, the length $L_M$ of the manifold layer 205 and the width W M of the manifold layer 205 may lie in a contraction plane where the manifold layer 205 is configured to radially contract in all directions in the contraction plane or a planar area defined by the first side 230 and/or the second side 235 of the manifold layer. For example, if the tissue interface 120 is not subjected to negative pressure, the length $L_M$ may be a nominal or relaxed length, and the width $W_M$ may be a nominal or relaxed width. In some embodiments, the length $L_M$ may be greater than the width $W_M$, such that the width $W_M$, may be less than the length $L_M$. For example, the tissue interface 120 may have an elongate shape. In some embodiments, for example, the tissue interface 120 may have a length $L_M$ to width $W_M$ ratio of at least 4:1. In some embodiments, the length $L_M$ may be equal to the width $W_M$. In some embodiments, the length $L_M$ may be less than the width $W_M$.

Although the manifold layer 205 is shown as having an elongate rectangular shape, the manifold layer 205 may have other shapes. For example, the manifold layer 205 may have a stadium, diamond, square, oval or circular shape. In some embodiments, the shape of the manifold layer 205 may be selected to accommodate the type of tissue site being treated. For example, the manifold layer 205 may have an oval or circular shape to accommodate an oval or circular tissue site. In other example embodiments, the manifold layer 205 may be resized and formed into any desirable shape by a clinician prior to placement at the tissue site.

As further illustrated in FIG. 3A, the holes 210 may include a first plurality of holes 315 in the first row 204 and a second plurality of holes 320 in the second row 206. Additional rows of holes may be provided, as shown in the non-limiting embodiment of FIG. 3A. Each of the first plurality of holes 315 and the second plurality of holes 320 may be configured to have an elongate shape that extends through the first side 230, the second side 235, and the thickness of the manifold layer 205.

In some embodiments, each of the first plurality of holes 315 and the second plurality of holes 320 may have a length that is longer than and perpendicular to a hole width. In some embodiments, each of the first plurality of holes 315 and the second plurality of holes 320 may have a shape configured to be a parallelogram. In some embodiments where the holes 210 are parallelogram-shaped, each of the first plurality of holes 315 may have a length $L_1$ and a width $W_1$ perpendicular to the length $L_1$, and each of the second plurality of holes 320 may have a length $L_2$ and a width $W_2$ perpendicular to the length $L_2$. In the example of FIG. 3A, $L_1$ and $L_2$ may be about 10-17 millimeters, and $W_1$ and $W_2$ may be about 3-8 millimeters. In some embodiments, the length $L_1$ may be equal to the length $L_2$. In some embodiments, the width $W_1$ may be equal to the width $W_2$. In other embodiments, $L_1$ and $L_2$ may be substantially equal, and $W_1$ and $W_2$ may be substantially equal, within acceptable manufacturing tolerances.

The first plurality of holes 315 and the second plurality of holes 320 may be distributed across the manifold layer 205 in one or more rows in one direction or in different directions. In some embodiments, the rows of the first plurality of holes 315 and the second plurality of holes 320 may be offset or staggered. In some embodiments, the length $L_1$ of one or more of the first plurality of holes 315 in the first row 204 may point toward the length $L_2$ of one or more of the second plurality of holes 320 in the second row 206. In some embodiments, the length $L_2$ of one or more of the second plurality of holes 320 in the second row 206 may point toward the length $L_1$ of one or more of the first plurality of holes 315 in the first row 204.

In some embodiments, the first plurality of holes 315 in the first row 204 may overlap with the second plurality of holes 320 in the second row 206. For example, at least a portion of the first plurality of holes 315 in the first row 204 would also be positioned or extend into the second row 206 and at least a portion of the second plurality of holes 320 in the second row 206 would also be positioned or extend into the first row 204. In other embodiments, the first plurality of holes 315 in the first row 204 may not overlap with the second plurality of holes 320 in the second row 206. For example, the first plurality of holes 315 may be positioned entirely in the first row 204 separate from the second plurality of holes 320 positioned entirely in the second row 206.

In some embodiments, the length L 1 of one or more of the first plurality of holes 315 in the first row 204 may be positioned at an angle relative to the length $L_2$ of one or more of the second plurality of holes 320 in the second row 206. In some embodiments, the length $L_1$ of one or more of the first plurality of holes 315 in the first row 204 may be angled toward the hole length $L_2$ of one or more of the second plurality of holes 320 in the second row 206. In some embodiments, the length $L_1$ of one or more of the first plurality of holes 315 in the first row 204 may form an angle of about 90 degrees relative to the length $L_2$ of one or more of the second plurality of holes 320 in the second row 206. In some embodiments, the length $L_1$ of one or more of the first plurality of holes 315 in the first row 204 may form an angle of about 45 degrees relative to the width $W_2$ of one or more of the second plurality of holes 320 in the second row 206.

In some embodiments, the first plurality of holes 315 in the first row 204 and the second plurality of holes 320 in the second row 206 may extend along the length $L_M$ of the manifold layer 205. In some embodiments, the length $L_1$ of the first plurality of holes 315 and the length $L_2$ of the second plurality of holes 320 may be positioned at an angle relative to the length $L_M$ of the manifold layer 205. For example, each of the first plurality of holes 315 may have a first long axis, such as a first reference line 325, which may be parallel to the length $L_1$ of the first plurality of holes 315. Each of the second plurality of holes 320 may have a second long axis, such as a second reference line 330, which may be parallel to the length $L_2$ of the second plurality of holes 320. In some embodiments, one or both of the first reference line 325 and the second reference line 330 may be defined relative to the length $L_M$. For example, the first reference line 325 may form a first angle 335 relative to the length $L_M$ and the second reference line 330 may form a second angle 340 relative to the length LAI. In some embodiments, the first angle 335 may be about 45° relative to the length $L_M$ and the second angle 340 may be about 135° relative to the length $L_M$. In some embodiments, the first angle may about 135° relative to the length $L_M$ and the second angle may be about 45° relative to the length LAI.

The pattern of holes 210 may be characterized by a pitch, which indicates the spacing between corresponding points on holes 210 within a pattern. In example embodiments, pitch may indicate the spacing between the centroids of holes 210 within the pattern. Some patterns may be characterized by a single pitch value, while others may be characterized by at least two pitch values. For example, if the spacing between centroids of the holes 210 is the same in all orientations, the pitch may be characterized by a single value indicating the spacing between centroids in adjacent rows. In some embodiments, a pattern comprising the first plurality of holes 315 and the second plurality of holes 320 may be characterized by two pitch values, $P_1$ and $P_2$. $P_1$ may be the spacing between the centroid of one or more of the first plurality of holes 315 and another of the first plurality of holes 315 in the first row 204 along the first orientation line 305. $P_2$ may be the spacing between the centroid of one or more of the first plurality of holes 315 in the first row 204 and one or more of the second plurality of holes 320 in the second row 206 perpendicular to the first orientation line 305. In some embodiments, $P_1$ may be about 18-22 millimeters and $P_2$ may be about 10-15 millimeters.

Figure 3B:
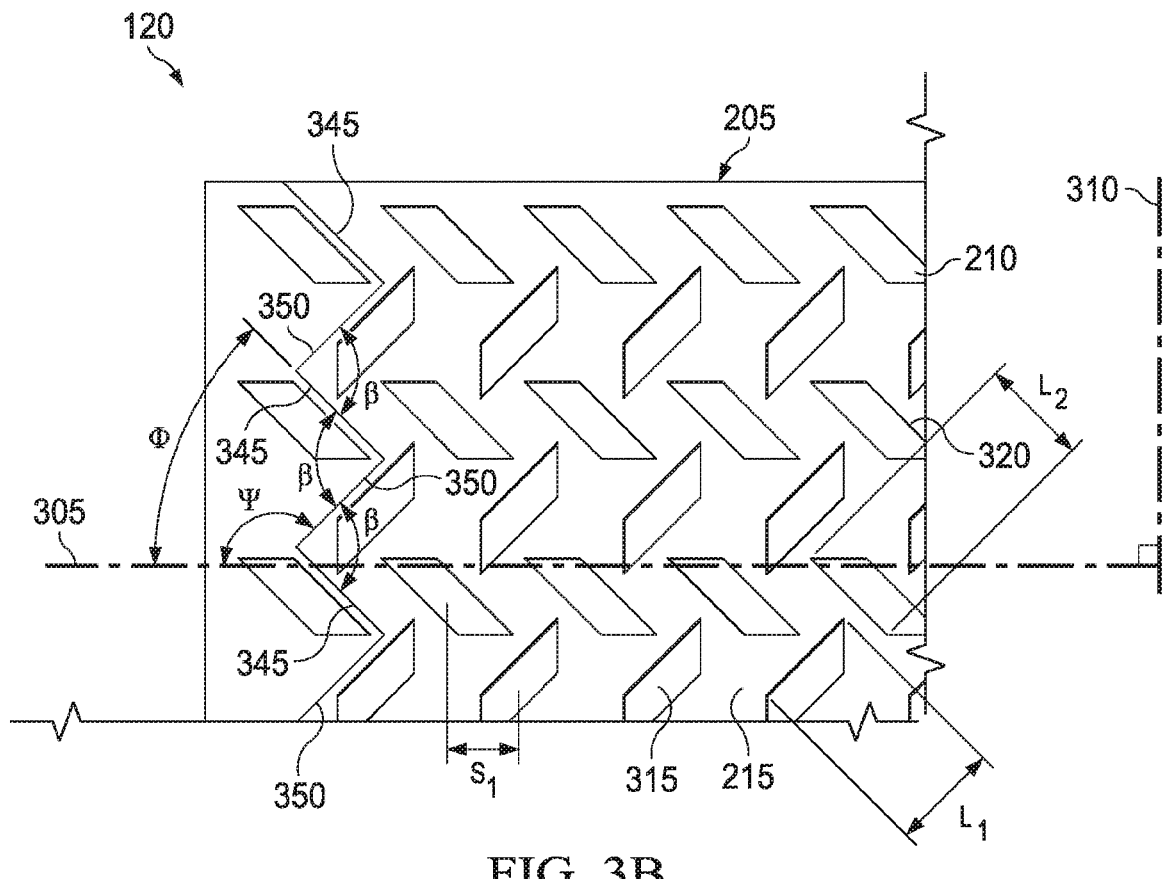
FIG. 3B is a detail view of the tissue interface of FIG. 3A taken at reference FIG. 3B in FIG. 3A.

FIG. 3B is a detail view of the manifold layer 205 taken at reference FIG. 3B in FIG. 3A. In some embodiments, the rows may be offset or staggered. The stagger may be characterized by an orientation of corresponding points in successive rows relative to an edge or other reference line associated with the manifold layer 205. In some embodiments, the rows of the first plurality of holes 315 may be staggered with the rows of the second plurality of holes 320. In some embodiments, the stagger may be characterized by a distance or a stagger value Si, where Si may be the spacing between the centroid of one or more of the first plurality of holes 315 in the first row 204 and one or more of the second plurality of holes 320 in the second row 206 in a direction parallel to the to the first orientation line 305.

In some embodiments, the plurality of walls 215 may form a web including a plurality of alternating first wall portions 345 and second wall portions 350. The first wall portions 345 may be oriented at an angle $\Phi$ with respect to the first orientation line 305. In the example of FIG. 3B, the first wall portions 345 may be about 45° with respect to the first orientation line 305. The second wall portions 350 may be oriented at an angle $\Psi$ with respect to the first orientation line 305. In the example of FIG. 3B, the second wall portions 350 may be about 135° with respect to the first orientation line 305. In some embodiments, the first wall portions 345 may be parallel to the length $L_1$ of the first plurality of holes 315, and the second wall portions 350 may be parallel to the length $L_2$ of the second plurality of holes 320. The first wall portions 345 and the second wall portions 350 may have an angle $\beta$ of about 90° between each wall portion.

Figure 4:
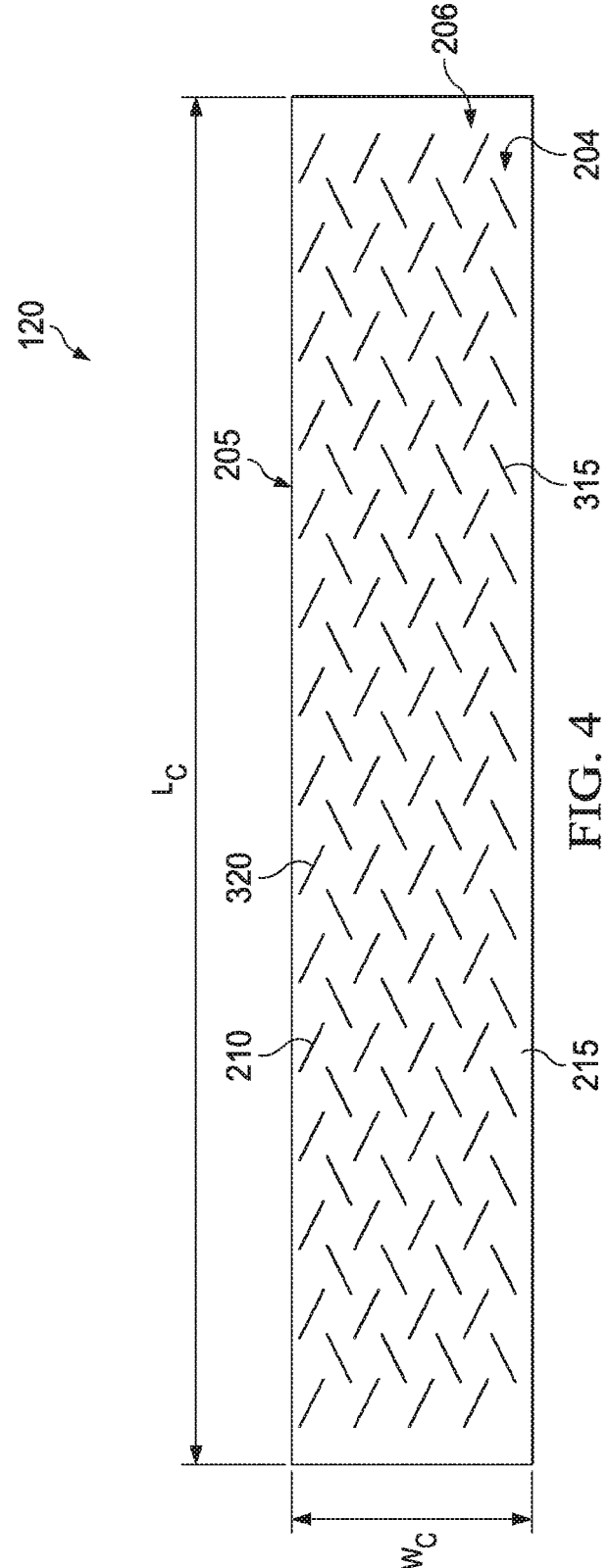
FIG. 4 is a top view of an example of a tissue interface under negative pressure.

FIG. 4 is a top view of an example of the manifold layer 205 of FIG. 2A in a contracted position, illustrating additional details that may be associated with some embodiments. As shown in FIG. 4, if negative pressure is applied to the tissue interface 120, the plurality of holes 210 of the manifold layer 205 may collapse or contract from a relaxed position to a contracted position. In some embodiments, the manifold layer 205 may be configured to contract to the contracted position when exposed to a reduced pressure of about −125 mm Hg. Contraction may occur in all directions as the holes 210 become smaller under the compressive force of negative pressure and apposition forces may be generated. The holes 210 aid in the delivery of negative pressure and the removal of fluids even when the holes 210 are collapsed. When instillation therapy is used, the holes 210 may also aid in the delivery of fluids even when contracted. Additionally, if negative pressure is applied to the tissue interface 120, the manifold layer 205 may collapse or contract to a contracted length and a contracted width, wherein the contracted length and the contracted width is less than a relaxed length and a relaxed width in the absence of negative pressure. Under an applied negative pressure, the tissue interface 120 may collapse or contract to a contracted length $L_C$ and a contracted width We that is less than the nominal or relaxed length $L_M$ and the nominal or relaxed width $W_M$ of the tissue interface 120. As the tissue interface 120 contracts, the contraction may be applied to the tissue site.

In some embodiments, the manifold layer 205 may comprise a first surface area when in the relaxed position and a second surface area when in the contracted position. In a contracted position, such as shown in FIG. 5, the second surface area may be between about 20-35 percent less than the first surface area. In some embodiments, the second surface area may be at least 20 percent less than the first surface area.

Figure 5A:
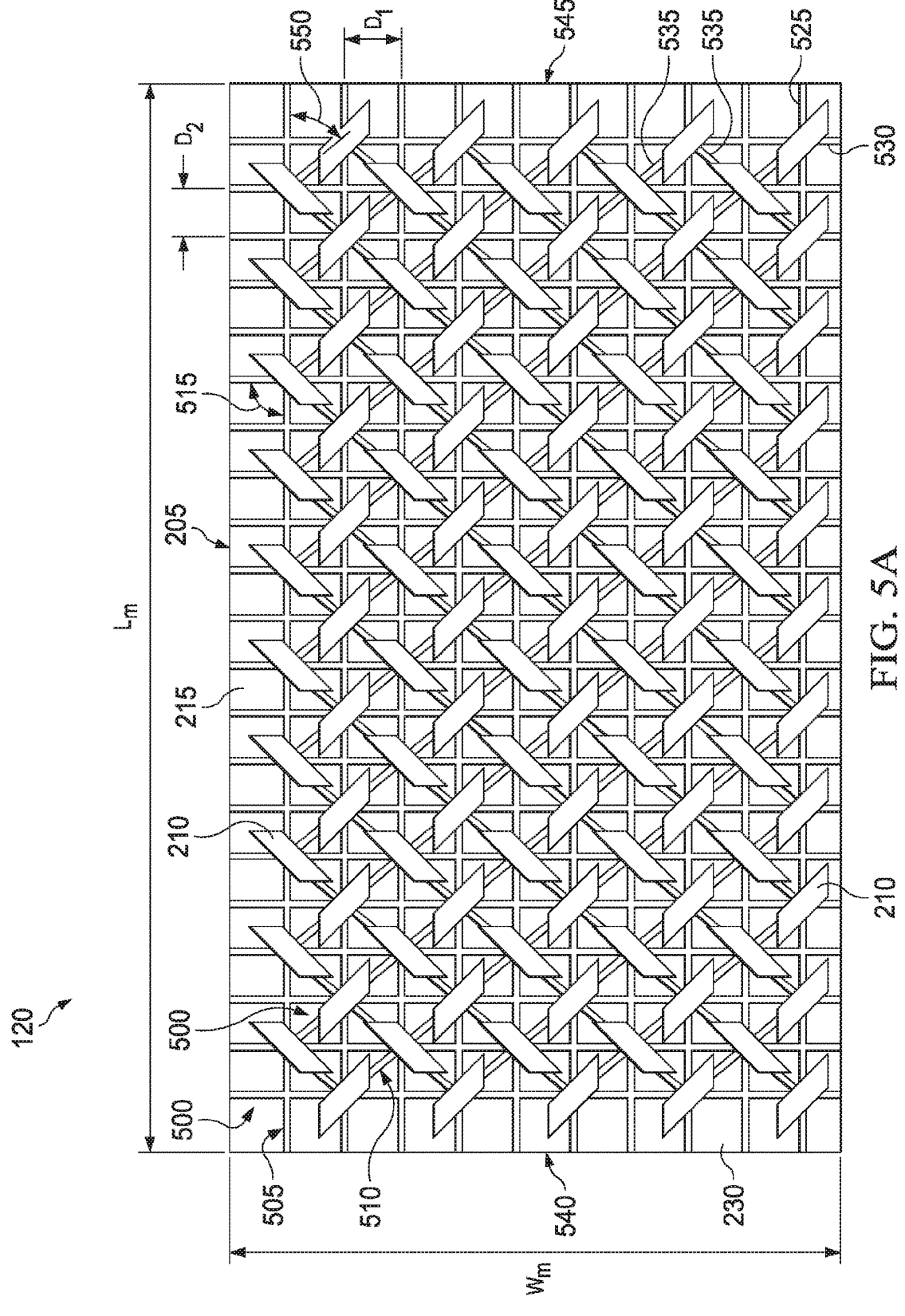
FIG. 5A is a top view of another example of a tissue interface that can be associated with some embodiments of the therapy system and the dressing of FIG. 1.

FIG. 5A is a top view of another example of a manifold layer 205 that can be associated with some embodiments of the tissue interface 120 of FIGS. 2A and 2B. In some embodiments, the manifold layer 205 may comprise at least one surface channel 500 having a channel length extending along at least one manifold surface or side of the manifold layer 205. For example, the channel length of the at least one surface channel 500 may extend along one or both of the first side 230 or the second side 235 of the manifold layer 205. In some embodiments, the at least one surface channel 500 may be a plurality of surface channels 500. In some embodiments, the plurality of surface channels 500 may also intersect the plurality of holes 210. The plurality of surface channels 500 may also intersect one another at an intersection angle 515 to form one or more grid patterns as described herein.

For example, the plurality of surface channels 500 may intersect to form a first grid 505 and a second grid 510. A first plurality of surface channels 525 and a second plurality of surface channels 530 of the plurality of surface channels 500 may intersect to form the first grid 505. In some embodiments, the first plurality of surface channels 525 and the second plurality of surface channels 530 of the first grid 505 may intersect to form the intersection angle 515. The intersection angle 515 may be about 90 degrees and form a square grid pattern. In some embodiments, the plurality of surface channels 500 may further comprise a third plurality of surface channels 535. The third plurality of surface channels 535 may intersect the first plurality of surface channels 525 and the second plurality of surface channels 530 to form the second grid 510. In some embodiments, the third plurality of surface channels 535 may intersect the first plurality of surface channels 525 and the second plurality of surface channels 530 at the same point where the first plurality of surface channels 525 and the second plurality of surface channels 530 intersect. In some embodiments, the third plurality of surface channels 535 may intersect the first grid 505 to form the second grid 510. The third plurality of surface channels 535 may intersect the first grid 505 at a grid angle 550. In some embodiments, the grid angle 550 may be about 45 degrees.

In some embodiments, the plurality of surface channels 500 may be spaced apart by a separation distance. For example, each of the first plurality of surface channels 525 may extend from a first end 540 of the manifold layer 205 to a second end 545 opposite the first end 540. In some embodiments, each of the first plurality of surface channels 525 may be spaced apart along the width $W_M$ of the manifold layer 205 by a distance $D_1$. The second plurality of surface channels 530 may be perpendicular to the first plurality of surface channels 525. In some embodiments, each of the second plurality of surface channels 530 may be spaced apart along the length $L_M$ of the manifold layer 205 by a distance $D_2$. In the example of FIG. 5A, $D_1$ and $D_2$ may be between about 8 millimeters to about 12 millimeters.

Figure 5B:
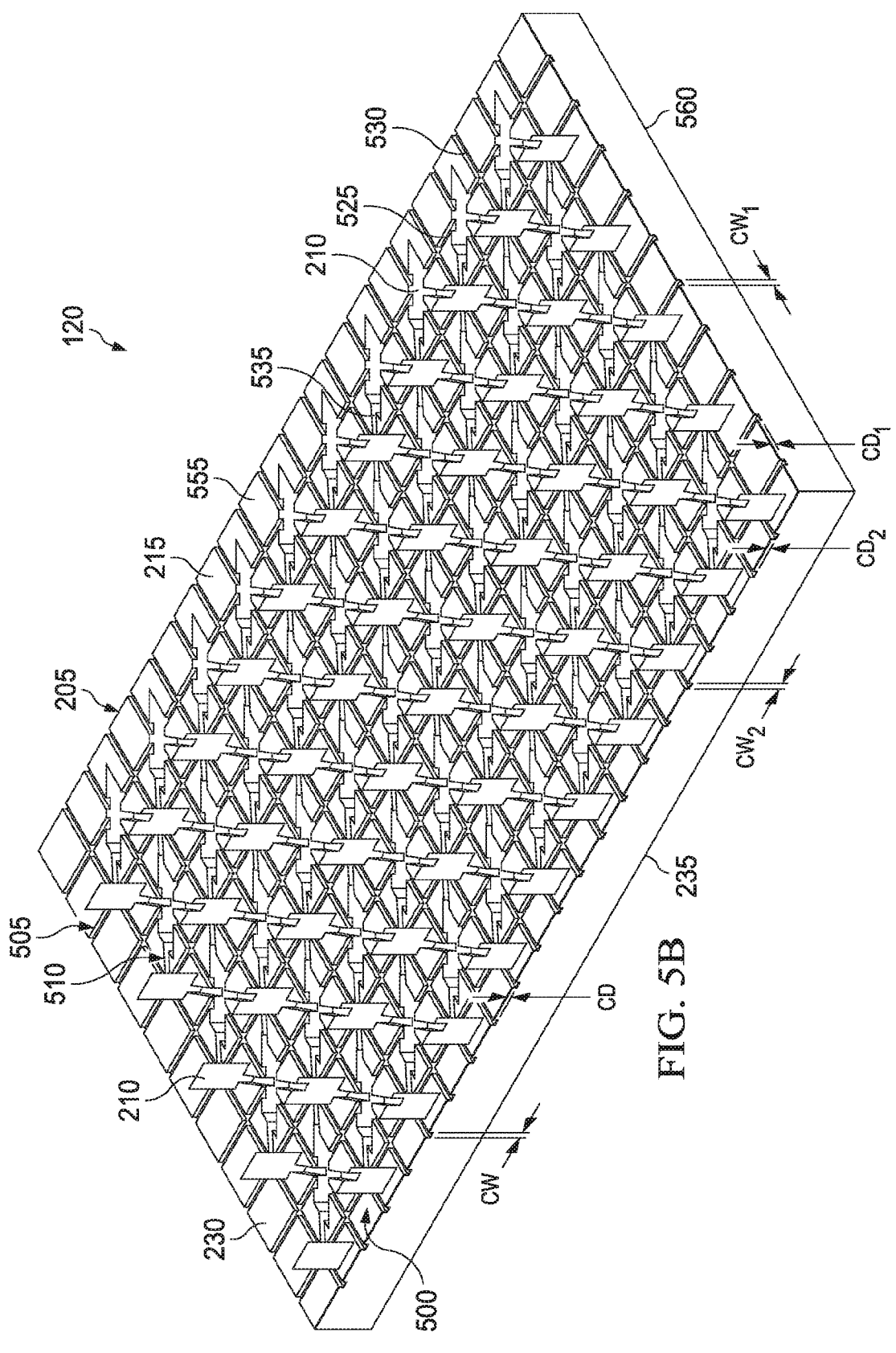
FIG. 5B is a perspective view of the tissue interface of FIG. 5A, illustrating additional features that may be associated with some embodiments.

FIG. 5B is a perspective view of the manifold layer 205 of FIG. 5A, illustrating additional details that may be associated with some embodiments. In some embodiments, the plurality of surface channels 500 may comprise a channel depth CD and a channel width CW perpendicular to the channel depth CD. The channel depth CD may extend into the thickness of the manifold layer 205 from a manifold surface, such as one or both of a first manifold surface 555 or a second manifold surface 560 opposite the first manifold surface 555. Although not shown in FIG. 5B, the plurality of surface channels 500 may be positioned on the second manifold surface 560 in addition to or in lieu of the plurality of surface channels 500 shown on the first manifold surface 555. In some embodiments, the channel depth CD may be between about 1 millimeter to about 8 millimeters and the channel width CW may be between about 0.5 millimeters to about 2 millimeters.

In some embodiments, the first plurality of surface channels 525 and the second plurality of surface channels 530 of the plurality of surface channels 500 may each have a first channel depth $CD_1$ and a second channel depth $CD_2$, respectively. In some embodiments, the second channel depth $CD_2$ is greater than the first channel depth $CD_1$ ($CD_2 > CD_1$). In some embodiments, the third plurality of surface channels 535 forming the second grid 510 may have a third channel depth $CD_3$ (not shown). In some embodiments, the first channel depth $CD_1$ and the second channel depth $CD_2$ may be equal so that the first plurality of surface channels 525 and the second plurality of surface channels 530 that form the first grid 505 have the same depth ($CD_2 = CD_1$). In some embodiments, the third channel depth $CD_3$ is greater than both first channel depth $CD_1$ and the second channel depth $CD_2$ so that the depth of the second grid 510 is greater than the depth of the first grid 505 ($CD_3 > [CD_2 = CD_1]$).

Figure 6A:
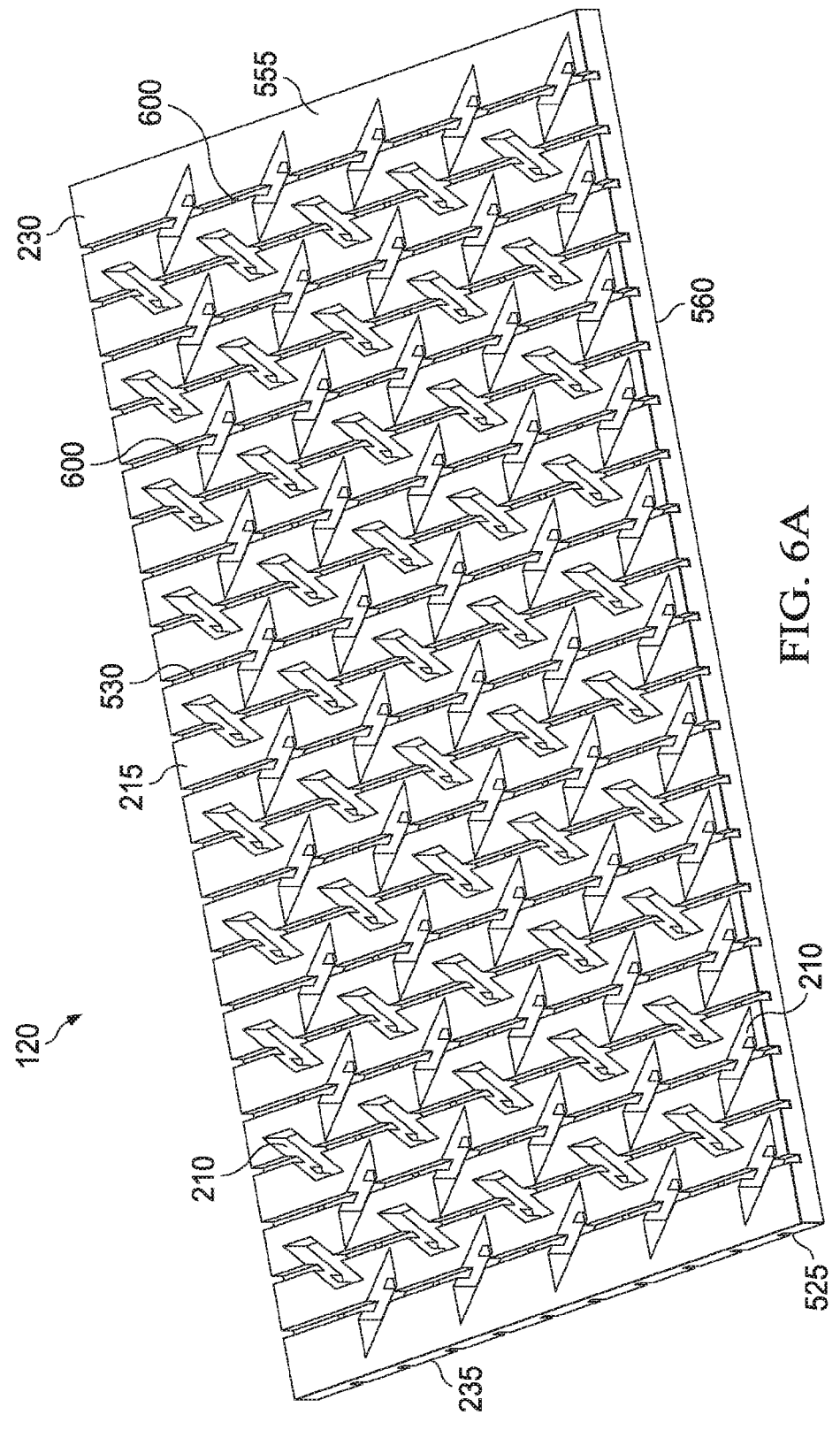
FIG. 6A is a perspective view of another example of a tissue interface that can be associated with the therapy system and the dressing of FIG. 1.

FIG. 6A is a perspective view of another example of a manifold layer 205 that can be associated with some embodiments of the tissue interface 120 of FIGS. 2A and 2B. In some embodiments, the plurality of surface channels 500 may extend along the first manifold surface 555 of the manifold layer 205. In some embodiments, the plurality of surface channels 500 may extend along both the first manifold surface 555 and the second manifold surface 560. For example, the second plurality of surface channels 530 may extend along the first manifold surface 555 and the first plurality of surface channels 525 may extend along the second manifold surface 560.

Figure 6B:
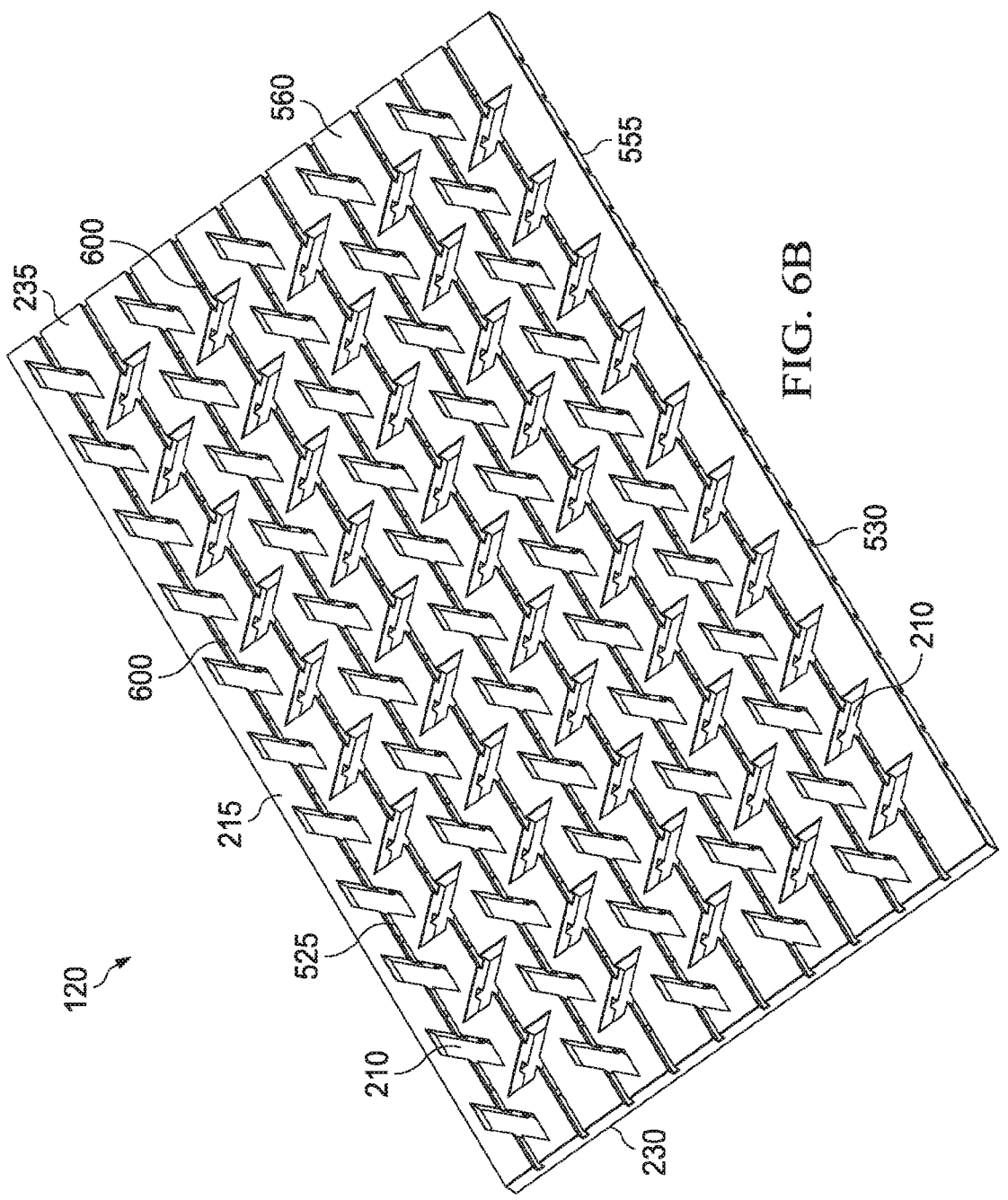
FIG. 6B is a perspective view of a second side of the tissue interface of FIG. 6A, illustrating additional features that may be associated with some embodiments.

FIG. 6B is a perspective view of the second side 235 of the tissue interface 120 of FIG. 6A, illustrating additional features that may be associated with some embodiments. In some embodiments, the first plurality of surface channels 525 may extend along the second manifold surface 560 at a 90 degree angle relative to the second plurality of surface channels 530 extending along the first manifold surface 555. Referring to FIGS. 6A and 6B, the second channel depth $CD_2$ of the second plurality of surface channels 530 may extend from the first manifold surface 555 toward the second manifold surface 560, and the first channel depth $CD_1$ of the first plurality of surface channels 525 may extend from the second manifold surface 560 toward the first manifold surface 555. In some embodiments, the first channel depth $CD_1$ may intersect with the second channel depth $CD_2$ to form a channel aperture 600 that extends through the first manifold surface 555, the second manifold surface 560, and the thickness of the manifold layer 205.

Figure 7:
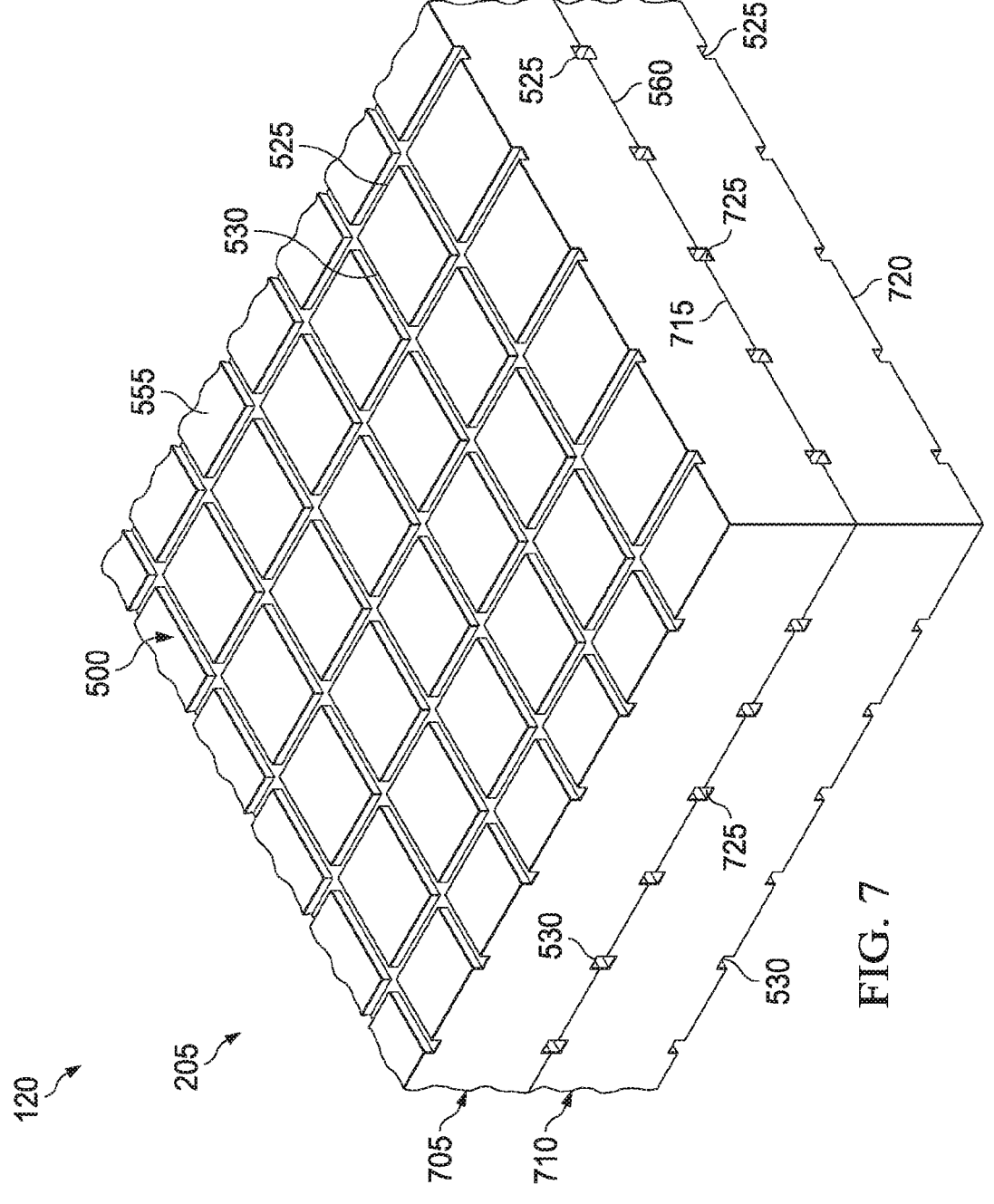
FIG. 7 is a perspective view of another example of a tissue interface that can be associated with the therapy system and the dressing of FIG. 1.

FIG. 7 is a perspective, side view of another example of a manifold layer 205 that can be associated with some embodiments of the tissue interface 120 of FIG. 1. In some embodiments, the manifold layer 205 may be formed by two or more layers. For example, the manifold layer 205 may comprise a first manifold layer 705 and a second manifold layer 710. Similar to embodiments of the manifold layer 205, the first manifold layer 705 may comprise the first manifold surface 555 and the second manifold surface 560. The second manifold layer 710 may comprise a third manifold surface 715 and a fourth manifold surface 720. In some embodiments, the first manifold surface 555, the second manifold surface 560, the third manifold surface 715, and the fourth manifold surface 720 may each comprise the plurality of surface channels 500 In some embodiments, the first manifold surface 555, the second manifold surface 560, the third manifold surface 715, and the fourth manifold surface 720 may each comprise the first plurality of surface channels 525 and the second plurality of surface channels 530.

In some embodiments, the first manifold layer 705 and the second manifold layer 710 may be bonded together to form the manifold layer 205. In some embodiments, the second manifold surface 560 of the first manifold layer 705 may be bonded to the third manifold surface 715 of the second manifold layer 710. In some embodiments, the first plurality of surface channels 525 on the second manifold surface 560 may be aligned with the first plurality of surface channels 525 on the third manifold surface 715, and the second plurality of surface channels 530 on the second manifold surface 560 may be aligned with the second plurality of surface channels 530 on the third manifold surface 715 to form at least one section channel 725 extending into the thickness of the manifold layer 205 substantially parallel to the first manifold surface 555, the second manifold surface 560, the third manifold surface 715, and the fourth manifold surface 720. In some embodiments, the at least one section channel may be a plurality of section channels 725. In other embodiments, the manifold layer 205 may be formed using a single layer, such as the manifold layer 205, and perforating the manifold layer 205 along the length and width of the manifold layer 205 to form the plurality of section channels 725.

In other embodiments, the manifold layer 205 may be a laminate of different densities of closed-cell foam. In such an embodiments, the manifold layer 205 may feel more flexible. In other embodiments, the laminate forming the manifold layer 205 may comprise three layers, such as two outer layers and an inner layer. The inner layer may be sandwiched between the outer layers. The outer layers may be stiffer than the inner layer, and the inner layer may be softer and more likely to conform. In still other embodiments, the manifold layer 205 may be perforated along its length and width through the closed-cell foam to provide lateral manifolding channels, such as the plurality of section channels 725. The plurality of section channels 725 may be formed by bonding at least two laminated layers where channels are thermoformed onto the surfaces of the laminated layers. The bonding process does not seal the channels closed. As a result, each thinner layer of closed-cell foam would be embossed on each side and then bonded to form a multi-orientation manifolding structure. Suitable adhesives for bonding include hot melts. The hot melts may be pattern coated onto the surfaces so as not to block the channels. In some embodiments, an adhesive may be sprayed onto the surfaces of the manifold layer 205. A fine mist of adhesive is unlikely to block the channels if the channels are about 2-3 millimeters deep. Additionally or alternatively, solvent borne adhesives may be used, such as acrylic or reactive polyurethanes. A form of heat lamination may also be used, where surface localized heat is applied to the foam layers to soften or tackify the bonding surfaces before pressing the foam layers together. Two-part reactive adhesives may also be used where one surface is coated with a first adhesive and another surface is coated with a second adhesive. The surfaces comprising the first adhesive and the second adhesive are then brought together to form the bond.

In other embodiments, one or both of the outer surfaces of the manifold layer 205 may include a texture. For example, one or both of the first manifold surface 555 and the fourth manifold surface 720 may include a texture. The texture may allow areas of the manifold layer 205 not containing channels to form manifolding areas. In some embodiments, the texture may comprise a random pattern of peaks, such as a tough Standex finish; a leather-effect patterns; a patterns of pyramids; a patterns of triangles; or a pattern of other shapes. Additionally or alternatively, one or both of the outer surfaces of the manifold layer 205 may be coated with hydrophilic or hydrophobic materials, for example by a plasma coating, to modify the fluid distribution properties of the manifold layer 205. In some embodiments, the channels of the manifold layer 205 may be specifically coated with hydrophilic or hydrophobic materials.

In still other embodiments, all or some of the layers forming the manifold layer 205 may be different colors. The differing colors may improve visualization of fluids, such as bleeding. A full range of colors may be used to form the manifold layer 205.

Figure 8:
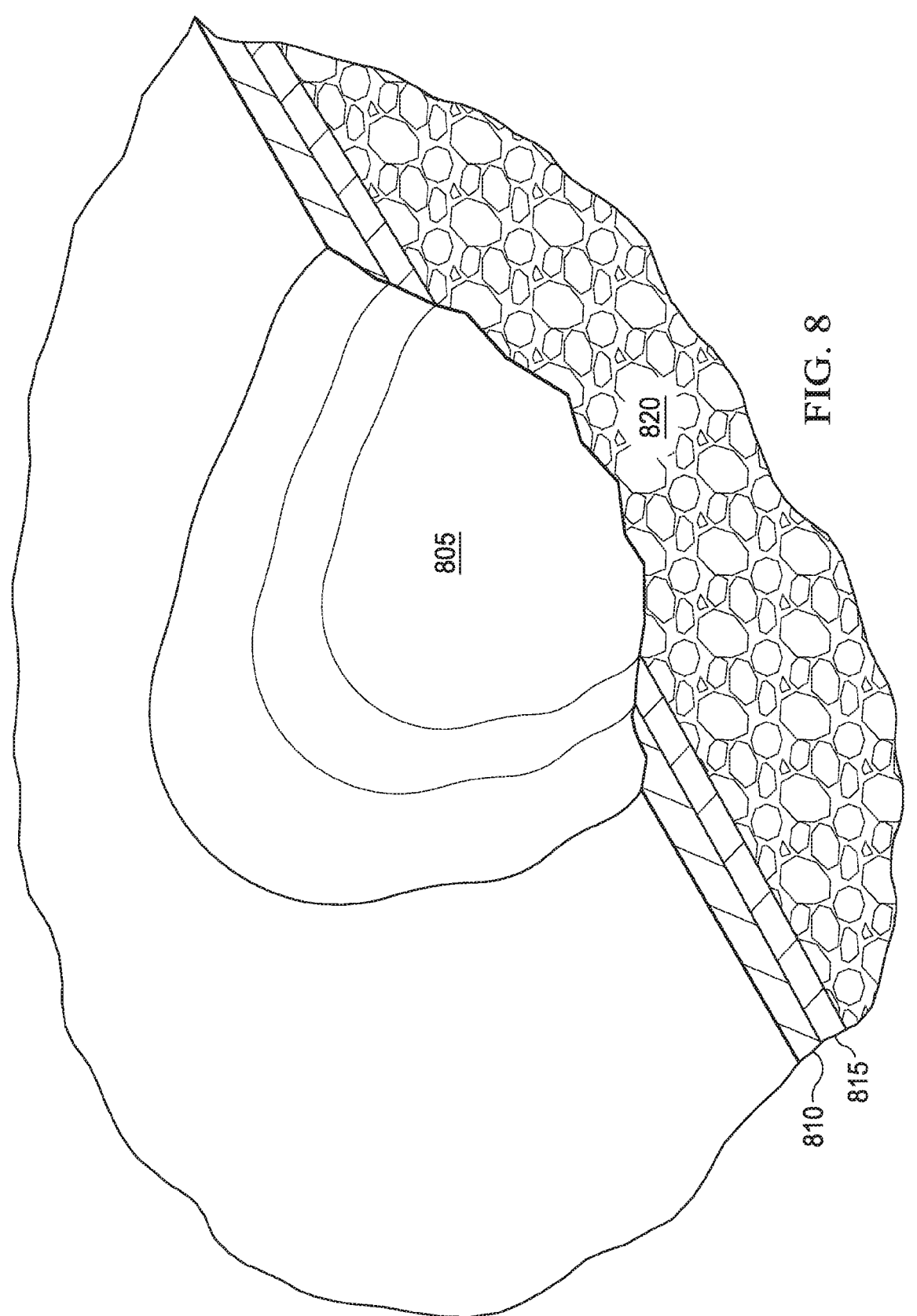
FIG. 8 is an isometric view, with a portion shown in cross-section, of an example tissue site.
Figure 9:
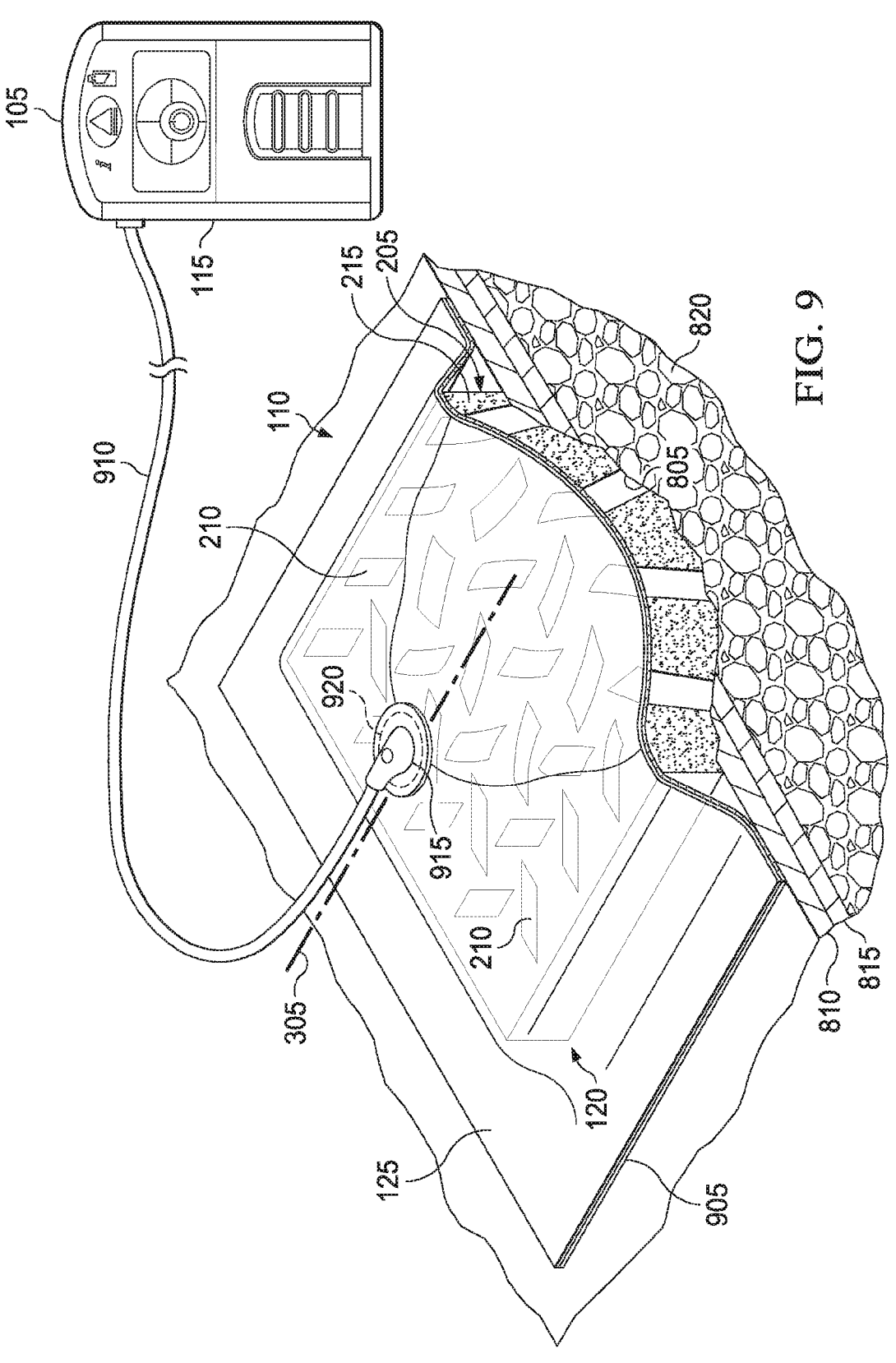
FIG. 9 is an isometric view, with a portion shown in cross-section, of a portion of an example embodiment of a therapy system and a dressing being deployed over an example tissue site.

Referring primarily to FIGS. 8 and 9, presented is an illustrative embodiment of a portion of the therapy system 100. FIGS. 8 and 9 depict the therapy system 100 assembled in stages at a tissue site 805, which may be a wound. In some embodiments, the tissue site 805 may be a deep wound. In some embodiments, the tissue site 805 may include a portion through an epidermis 810, dermis 815, and subcutaneous tissue 820. Referring now to FIG. 9, the dressing 110 may be disposed within the tissue site 805. The geometry and dimensions of the tissue interface 120, the cover 125, or both may vary to suit a particular application or anatomy. For example, the dressing 110 may be cut to size for a specific region or anatomical area. The dressing 110 may be cut without losing pieces of the tissue interface 120 and without separation of the tissue interface 120. In other embodiments, the dressing 110 may be placed proximate to the tissue site 805.

The tissue interface 120 can be placed in, over, on, or otherwise proximate to the tissue site 805. The manifold layer 205 may be cut to size, folded, and rolled into the tissue site 805. In some embodiments, the cover 125 may be placed over the manifold layer 205. The cover 125 may be configured to create a sealed space containing the manifold layer 205 at the tissue site. The negative-pressure source 105 may be configured to be positioned in fluid communication with the sealed space and the manifold layer 205 through the cover 125.

In some examples, the dressing 110 may include one or more attachment devices. In some embodiments, one or more of the attachment devices may include an adhesive 905. In some examples the adhesive 905 may be, for example, a medically-acceptable, pressure-sensitive adhesive that extends about a periphery, a portion, or an entire surface of each of the cover 125. In some embodiments, for example, the adhesive 905 may be an acrylic adhesive having a coating weight between 25-65 grams per square meter (g.s.m.). Thicker adhesives, or combinations of adhesives, may be applied in some embodiments to improve the seal and reduce leaks. In some embodiments, such a layer of the adhesive 905 may be continuous or discontinuous. Discontinuities in the adhesive 905 may be provided by apertures or holes (not shown) in the adhesive 905. The apertures or holes in the adhesive 905 may be formed after application of the adhesive 905 or by coating the adhesive 905 in patterns on a carrier layer, such as, for example, a side of the cover 125. Apertures or holes in the adhesive 905 may also be sized to enhance the MVTR of the adhesive 905 in some example embodiments.

The adhesive 905 can be disposed on a bottom side of the cover 125, and the adhesive 905 may pressed onto the cover 125 and epidermis 810 (or other attachment surface) to fix the dressing 110 in position and to seal the tissue interface 120 over the patient. In some embodiments, the adhesive 905 can be disposed only around edges of the cover 125.

FIG. 9 also illustrates one example of a fluid conductor 910 and a dressing interface 915. As shown in the example of FIG. 9, the fluid conductor 910 may be a flexible tube, which can be fluidly coupled on one end to the dressing interface 915. The dressing interface 915 may be an elbow connector. In some examples, the tissue interface 120 can be applied to the tissue site before the cover 125 is applied over the tissue interface 120. The cover 125 may include an aperture 920, or the aperture 920 may be cut into the cover 125 before or after positioning the cover 125 over the tissue interface 120. The position of the aperture 920 may be off-center or adjacent to an end or edge of the cover 125. In other examples, the aperture 920 may be centrally disposed. The dressing interface 915 can be placed over the aperture 920 to provide a fluid path between the fluid conductor 910 and the tissue interface 120. In other examples, the fluid conductor 910 may be inserted directly through the cover 125 into the tissue interface 120.

If not already configured, the dressing interface 915 may be disposed over the aperture 920 and attached to the cover 125. The fluid conductor 910 may be fluidly coupled to the dressing interface 915 and to the negative-pressure source 105.

Negative pressure from the negative-pressure source 105 can be distributed through the fluid conductor 910 and the dressing interface 915 to the tissue interface 120. The dressing 110 may be a bolster to aid in closing the tissue site 805. The tissue interface 120 may contract in response to the application of negative pressure. In some embodiments, the manifold layer 205 of the tissue interface 120 is configured to contract. For example, under an applied negative pressure, the manifold layer 205 may contract radially in all directions.

FIG. 10 is a table illustrating an improved percentage of collapse of the tissue interface 120 according to this disclosure. Testing was performed on manifolds comprising a plurality of holes shaped like an oval, a star, a parallelogram, and a parallelogram with overlapping perforations. The testing measured the percent collapse of each of the manifolds under negative pressure (about −125 mm Hg). The percentage of collapse is generally between about 20% and 30% of the initial area of the manifold. However, the percentage of collapse of a manifold with holes shaped like a parallelogram and a manifold with holes shaped like a parallelogram with overlapping perforations in accordance with this disclosure resulted in a collapse of 32.05% and 35.51%, respectively, higher than any other tested shapes or patterns.

Figure 11:
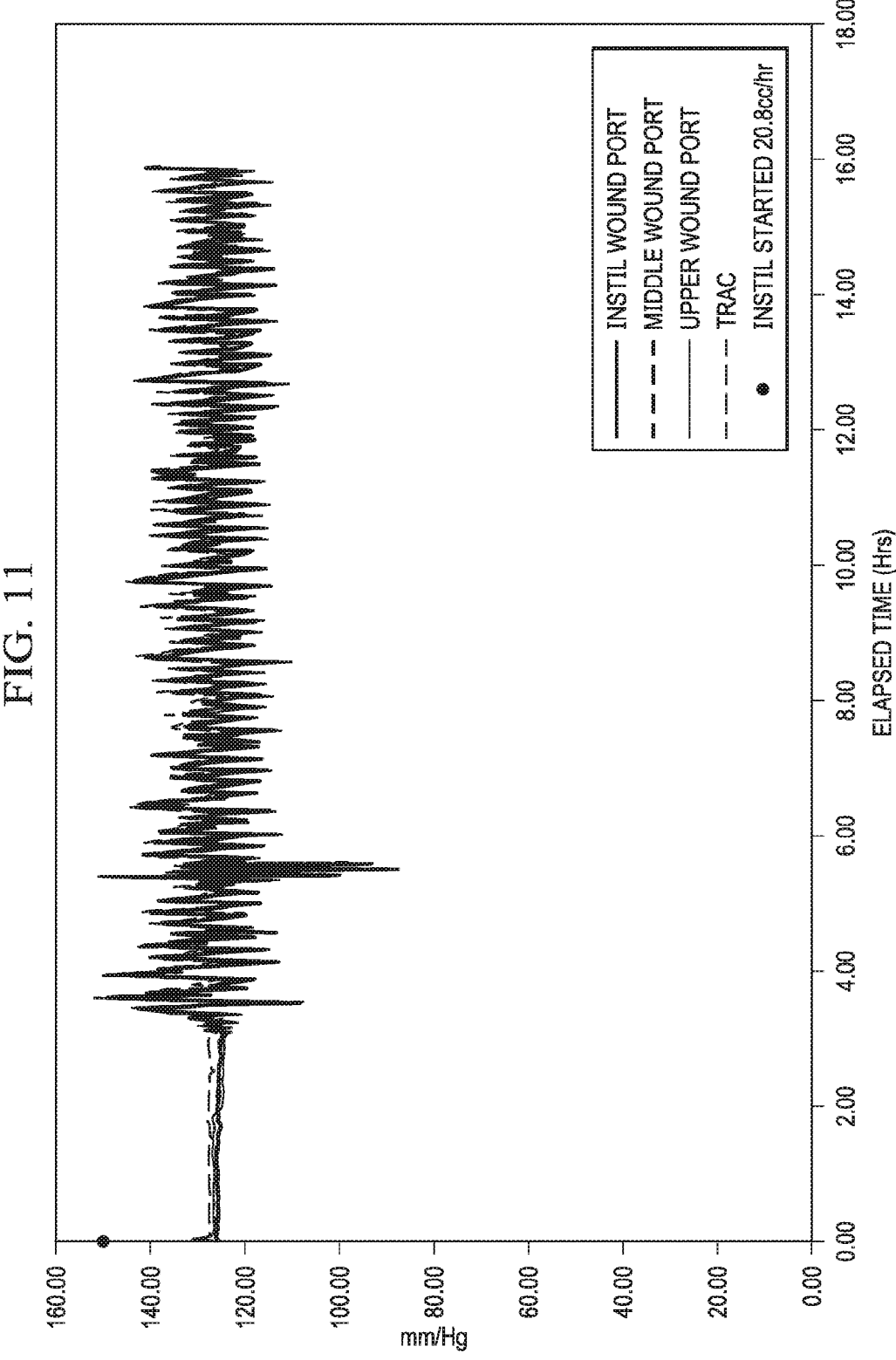
FIG. 11 is a graph of negative pressure measured at four locations in a sealed environment formed by the dressing of FIG. 1 plotted versus time, illustrating a range of reduced-pressure being maintained at all four locations.

FIG. 11 is a graph of negative pressure measured at four locations in a sealed environment formed by the dressing 110 of FIG. 1 plotted versus time, illustrating a range of reduced-pressure being maintained at all four locations. In the testing apparatus associated with the graph of FIG. 11, the tissue interface 120 was fluidly coupled to a system capable of providing both negative-pressure therapy and instillation therapy. The tissue interface 120 was monitored during negative-pressure and instillation cycles by pressure sensors in fluid communication with the sealed environment at four locations: an instillation port; a dressing interface, such as the dressing interface 915; a middle port disposed at the center of the tissue interface 120; and an upper port disposed on the tissue interface 120 at an opposite side from the dressing interface 915. During testing, fluid was infused at a rate of about 7.1 cc/hour and continuous negative pressure at about −125 mm Hg was suppled at the dressing interface.

A method of manufacturing the manifold layer 205 is also disclosed. The method may comprise cutting a plurality of patterns into a foam layer and felting a foam. The method may further comprise perforating the foam layer along the plurality of patterns. In some embodiments, a cutting tool may be used to perforate the foam layer. The method may further include extracting the perforated material from the foam layer. In some embodiments, a high flow vacuum system may be used to extract the perforated material from the foam layer.

The systems, apparatuses, and methods described herein may provide significant advantages. The manifold layer 205 is able to collapse radially in all directions, is easily conformable, and can be worn for an extended period of time without experiencing tissue in-growth. Specifically, the plurality of holes 210 shaped like parallelograms in the manifold layer 205 enable the manifold layer 205 to collapse radially in all directions. This improves fluid and pressure manifolding through the manifold layer 205 to the tissue interface 120. The radial collapse also draws the edges of the wound together and reduces the overall wound size.

The plurality of holes 210 in the manifold layer 205 make the manifold layer 205 easier to size, with or without tools. The manifold layer 205 is also flexible and conformable to enable a user to push the manifold layer 205 into deep and undermined spaces.

Additionally, the manifold layer 205 prevents tissue ingrowth. The manifold layer 205 also has a higher tensile strength than standard foam fillers to prevent materials from being left in the wound after the manifold layer 205 is removed.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be separated from other components for manufacture or sale. In other example configurations, the controller 130 may also be manufactured, configured, assembled, or sold independently of other components.

The appended claims set forth novel and inventive aspects of the subject matter described above, in this detailed description. Certain features, elements, or aspects may be omitted from the detailed description if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site, comprising;

a manifold layer including a first side configured to face the tissue site, a second side opposite the first side, and a thickness between the first side and the second side, the manifold layer comprising foam including a 25% compression load deflection between about 1.8 to about 2.8 pounds per square inch and pores having an average pore size between about 50 microns to about 120 microns;

a plurality of holes extending through the first side, the second side, and the thickness of the manifold layer and being positioned at least in a first row and a second row that is offset from the first row, each of the plurality of holes including a hole length that is longer than and perpendicular to a hole width, the hole length of at least one of the holes in the first row being positioned at an angle relative to the hole length of another of the holes in the second row; and a plurality of surface channels having a channel length extending along at least one manifold surface of the manifold layer, the plurality of surface channels having a channel depth and a channel width perpendicular to the channel length, wherein the channel depth extends partially into the thickness of the manifold layer from the manifold surface and the channel width extends perpendicular to the channel depth, and wherein the plurality of surface channels intersect the plurality of holes.

2. The dressing of claim 1, wherein the foam of the manifold layer has a density between about 6.5 lb/ft3 to about 12.8 lb/ft3.

3. The dressing of claim 1, wherein the foam of the manifold layer has a porosity between about 200 pores per inch to about 400 pores per inch.

4. The dressing of claim 1, wherein the thickness of the manifold layer is between about 8 millimeters to about 16 millimeters.

5. The dressing of claim 1, wherein each of the plurality of holes has a shape configured as a parallelogram.

6. The dressing of claim 1, wherein the hole length of one or more of the plurality of holes in the first row is angled toward the hole length of one or more of the plurality of holes in the second row.

7. The dressing of claim 1, wherein the hole length of one or more of the plurality of holes in the first row forms an angle of about 90 degrees relative to the hole length of one or more of the plurality of holes in the second row.

8. The dressing of claim 1, wherein plurality of holes in the first row and the second row extend along a manifold length of the manifold layer, wherein the hole length of one or more of the plurality of holes in the first row is positioned at a first angle of about 45 degrees relative to the manifold length, and wherein the hole length of one or more of the plurality of holes in the second row is positioned at a second angle of about 135 degrees relative to the manifold length.

9. The dressing of claim 1, wherein the plurality of surface channels intersect one another at an intersection angle to form a grid pattern.

10. The dressing of claim 9, wherein the intersection angle is about 90 degrees, and wherein the grid pattern is a square grid.

11. The dressing of claim 9, wherein the grid pattern is a first grid pattern, and wherein the plurality of surface channels intersect one another to form a second grid pattern that intersects the first grid pattern at a grid angle.

12. The dressing of claim 11, wherein the plurality of surface channels in the first grid pattern have a first channel depth and the plurality of surface channels in the second grid pattern have a second channel depth, and wherein the second channel depth is greater than the first channel depth.

13. The dressing of claim 1, wherein the channel depth of at least one of the surface channels is a first channel depth and the channel depth of another of the surface channels on the same manifold surface is a second channel depth, and wherein the second channel depth is greater than the first channel depth.

14. The dressing of claim 1, wherein the at least one manifold surface is the first side and the second side of the manifold layer, wherein the plurality of surface channels extend along the first side and the second side of the manifold layer, and wherein the surface channels on the first side are positioned at an angle relative to the surface channels on the second side.

15. The dressing of claim 14, wherein one or more of the surface channels on the first side has a first channel depth extending partially into the thickness of the manifold layer from the first side and one or more of the surface channels on the second side has a second channel depth extending partially into the thickness of the manifold layer from the second side, and wherein the first channel depth intersects the second channel depth to form a channel aperture that extends through the first side, the second side, and the thickness of the manifold layer.

16. The dressing of claim 1, further comprising at least one section channel extending into the thickness of the manifold layer substantially parallel to the first side and the second side of the manifold layer.

17. The dressing of claim 1, further comprising a contact layer configured to be positioned between the manifold layer and the tissue site and comprising a plurality of perforations disposed through opposing surfaces of the contact layer.

18. A system for treating a tissue site with reduced pressure, comprising:

a dressing according to claim 1;

a cover configured to create a sealed space containing the manifold layer at the tissue site; and a reduced-pressure source configured to be positioned in fluid communication with the sealed space and the manifold layer through the cover.

19. A dressing for treating a tissue site with negative pressure, the dressing comprising:

a manifold layer comprising foam and including a first side configured to face the tissue site, a second side opposite the first side, and a thickness between the first side and the second side;

a plurality of holes extending through the first side, the second side, and the thickness of the manifold layer and being positioned at least in a first row and a second row that is offset from the first row, each of the plurality of holes including a hole length that is longer than and perpendicular to a hole width, the hole length of at least one of the holes in the first row being positioned at an angle relative to the hole length of another of the holes in the second row; and a plurality of surface channels having a channel length extending along the first side and the second side of the manifold layer, wherein the surface channels on the first side are positioned at an angle relative to the surface channels on the second side, wherein one or more of the surface channels on the first side has a first channel depth extending partially into the thickness of the manifold layer from the first side and one or more of the surface channels on the second side has a second channel depth extending partially into the thickness of the manifold layer from the second side, and wherein the first channel depth intersects the second channel depth to form a channel aperture that extends through the first side, the second side, and the thickness of the manifold layer.

20. The dressing of claim 19, wherein the foam of the manifold layer has a porosity of about 200 pores per inch to about 400 pores per inch.

21. The dressing of claim 19, wherein the hole length of one or more of the plurality of holes in the first row is angled toward the hole length of one or more of the plurality of holes in the second row.

22. The dressing of claim 19, wherein the plurality of surface channels intersect one another at an intersection angle to form a grid pattern on at least one of the first side and the second side of the manifold layer, and wherein the plurality of surface channels intersect the plurality of holes.

23. The dressing of claim 22, wherein the grid pattern is a first grid pattern, and wherein the plurality of surface channels intersect one another to form a second grid pattern that intersects the first grid pattern at a grid angle.

24. The dressing of claim 23, wherein the plurality of surface channels in the first grid pattern have a different depth than the plurality of surface channels in the second grid pattern.

25. The dressing of claim 19, further comprising at least one section channel extending into the thickness of the manifold layer substantially parallel to the first side and the second side of the manifold layer.

\* \* \* \* \*